US010603129B2

(12) United States Patent
Roberson et al.

(10) Patent No.: US 10,603,129 B2
(45) Date of Patent: Mar. 31, 2020

(54) ULTRASONIC SURGICAL INSTRUMENT WITH INTEGRAL TORQUE WRENCH AND LONGITUDINAL ENGAGEMENT

(71) Applicant: ETHICON ENDO-SURGERY, LLC, Guaynabo, PR (US)

(72) Inventors: Eric Roberson, Cincinnati, OH (US); Stephen M. Leuck, Cincinnati, OH (US); William D. Dannaher, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 564 days.

(21) Appl. No.: 15/378,391

(22) Filed: Dec. 14, 2016

(65) Prior Publication Data

US 2018/0161057 A1 Jun. 14, 2018

(51) Int. Cl.
*A61B 18/18* (2006.01)
*A61B 90/00* (2016.01)
(Continued)

(52) U.S. Cl.
CPC ...... *A61B 90/03* (2016.02); *A61B 17/320068* (2013.01); *A61N 7/02* (2013.01);
(Continued)

(58) Field of Classification Search
CPC ...... A61B 17/00234; A61B 17/320068; A61B 17/320092; A61B 2017/00477;
(Continued)

(56) References Cited

U.S. PATENT DOCUMENTS 5,322,055 A 6/1994 Davison et al.
5,873,873 A 2/1999 Smith et al.
(Continued)

OTHER PUBLICATIONS

International Search Report and Written Opinion dated Feb. 13, 2018 for Application No. PCT/US2017/063854, 10 pgs.
(Continued)

*Primary Examiner* — Michael F Peffley
*Assistant Examiner* — Amanda L Zink
(74) *Attorney, Agent, or Firm* — Frost Brown Todd LLC

(57) ABSTRACT

A surgical instrument includes an instrument body, an ultrasonic transducer assembly, and a slip lock having an arrester. The transducer assembly is rotatably mounted along a longitudinal axis within the body such that the transducer assembly is configured to selectively rotate. The arrester is configured to move relative to the ultrasonic transducer assembly between an engaged position and a disengaged position and has a catch portion and a deflectable portion. The catch portion is configured to seize the transducer assembly and selectively inhibit rotation for rotatably coupling with the acoustic waveguide up to a predetermined torque. The deflectable portion is configured to deflect relative to the transducer assembly upon receiving a torque greater than the predetermined torque. Accordingly, the catch portion releases the transducer assembly to slip relative to the catch portion for limiting coupling of the transducer assembly with the acoustic waveguide to the predetermined torque.

20 Claims, 19 Drawing Sheets

(51) Int. Cl.
*A61N 7/02* (2006.01)
*A61B 17/32* (2006.01)
*A61B 18/00* (2006.01)
*A61B 17/00* (2006.01)

(52) U.S. Cl.
CPC .............. *A61B 2017/00477* (2013.01); *A61B 2017/320071* (2017.08); *A61B 2017/320094* (2017.08); *A61B 2017/320095* (2017.08); *A61B 2018/0063* (2013.01); *A61B 2018/00345* (2013.01); *A61B 2018/00601* (2013.01); *A61B 2018/00619* (2013.01); *A61B 2090/031* (2016.02)

(58) Field of Classification Search
CPC ....... A61B 2017/320069; A61B 2017/320094; A61B 2018/00345; A61B 2018/00601; A61B 2018/00619; A61B 2018/0063; A61B 2090/031; A61B 90/03; A61N 7/02
See application file for complete search history.

(56) References Cited

U.S. PATENT DOCUMENTS

| | | |
|---|---|---|
| 5,897,523 A | 4/1999 | Wright et al. |
| 5,980,510 A | 11/1999 | Tsonton et al. |
| 5,989,264 A | 11/1999 | Wright |
| 6,063,098 A | 5/2000 | Houser et al. |
| 6,090,120 A | 7/2000 | Wright et al. |
| 6,325,811 B1 | 12/2001 | Messerly |
| 6,454,782 B1 | 9/2002 | Schwemberger |
| 6,589,200 B1 | 7/2003 | Schwemberger et al. |
| 6,752,815 B2 | 6/2004 | Beaupre |
| 6,773,444 B2 | 8/2004 | Messerly |
| 6,783,524 B2 | 8/2004 | Anderson et al. |
| 7,135,030 B2 | 11/2006 | Schwemberger et al. |
| 7,621,930 B2 | 11/2009 | Houser |
| 8,461,744 B2 | 6/2013 | Wiener et al. |
| 8,591,536 B2 | 11/2013 | Robertson |
| 8,623,027 B2 | 1/2014 | Price et al. |
| 8,986,302 B2 | 3/2015 | Aldridge et al. |
| 9,023,071 B2 | 5/2015 | Miller et al. |
| 9,095,367 B2 | 8/2015 | Olson et al. |
| 9,381,058 B2 | 7/2016 | Houser et al. |
| 9,393,037 B2 | 7/2016 | Olson et al. |
| 9,402,682 B2 | 8/2016 | Worrell et al. |
| 9,408,622 B2 | 8/2016 | Stulen et al. |
| 9,872,699 B2 | 1/2018 | Boudreaux et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2012/0116265 A1 | 5/2012 | Houser et al. |
| 2015/0080924 A1 | 3/2015 | Stulen et al. |
| 2015/0245850 A1* | 9/2015 | Hibner ............ A61B 17/32009 606/171 |
| 2015/0265309 A1* | 9/2015 | Boudreaux ...... A61B 17/32009 606/169 |
| 2016/0015419 A1 | 1/2016 | Hibner et al. |

OTHER PUBLICATIONS

U.S. Appl. No. 61/410,603, filed Nov. 5, 2010.
U.S. Appl. No. 14/258,179, filed Apr. 22, 2014.
U.S. Appl. No. 15/378,414, filed Dec. 14, 2016.
U.S. Appl. No. 15/378,432, filed Dec. 14, 2016.
U.S. Appl. No. 15/378,452, filed Dec. 14, 2016.

\* cited by examiner

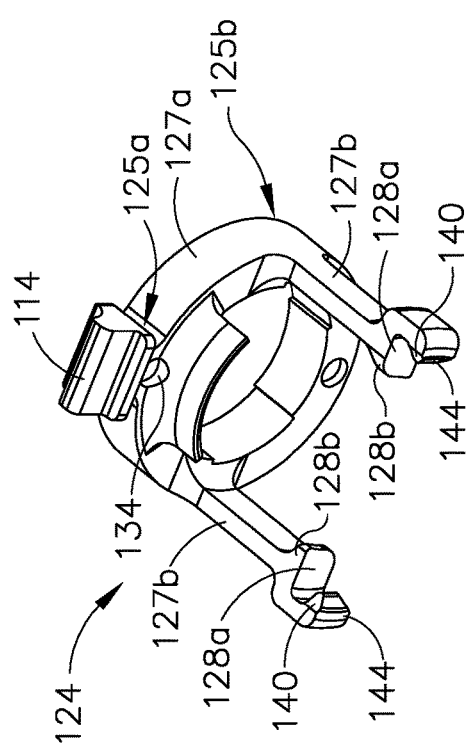
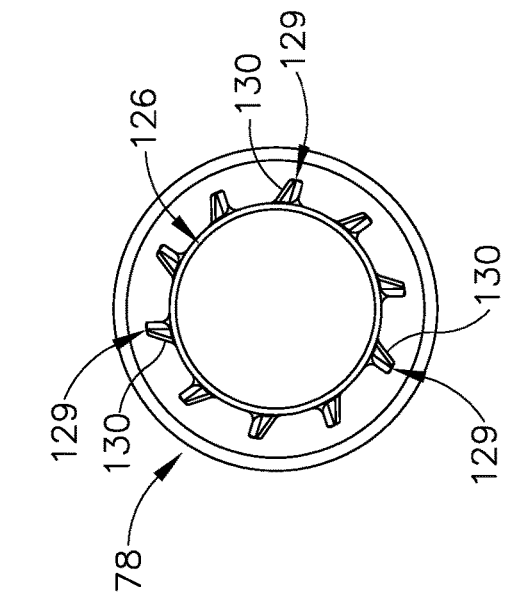
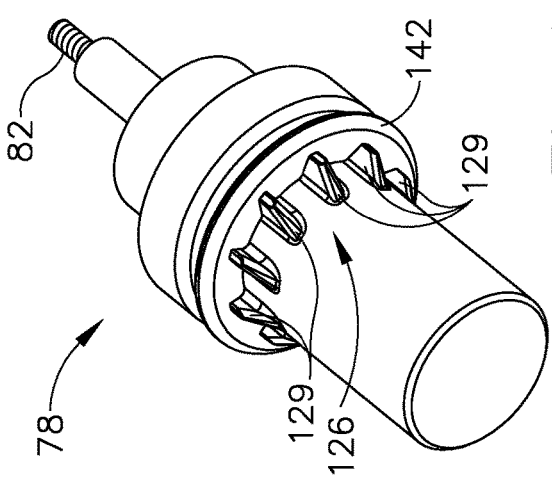

ULTRASONIC SURGICAL INSTRUMENT WITH INTEGRAL TORQUE WRENCH AND LONGITUDINAL ENGAGEMENT

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein, U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; U.S. Pub. No. 2014/0005703, entitled "Surgical Instruments with Articulating Shafts," published Jan. 2, 2014, issued as U.S. Pat. No. 9,408,622 on Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein; U.S. Pub. No. 2015/0080924, entitled "Articulation Features for Ultrasonic Surgical Instrument," published Mar. 19, 2015, issued as U.S. Pat. No. 10,172,636 on Jan. 8, 2019, the disclosure of which is incorporated by reference herein; and U.S. patent application Ser. No. 14/258,179, entitled "Ultrasonic Surgical Device with Articulating End Effector," filed Apr. 22, 2014, now Provisional App. No. 62/176,880, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 10 depicts a distal perspective view of a lock switch and an arrester of the proximal detent cam slip lock of FIG. 8;

FIG. 11 depicts a distal perspective view of the ultrasonic transducer assembly connected with an engagement collar and a detent flange of the of the proximal detent cam slip lock of FIG. 8;

FIG. 12 depicts a distal end elevational view of the ultrasonic transducer assembly of FIG. 8;

Figure 1:
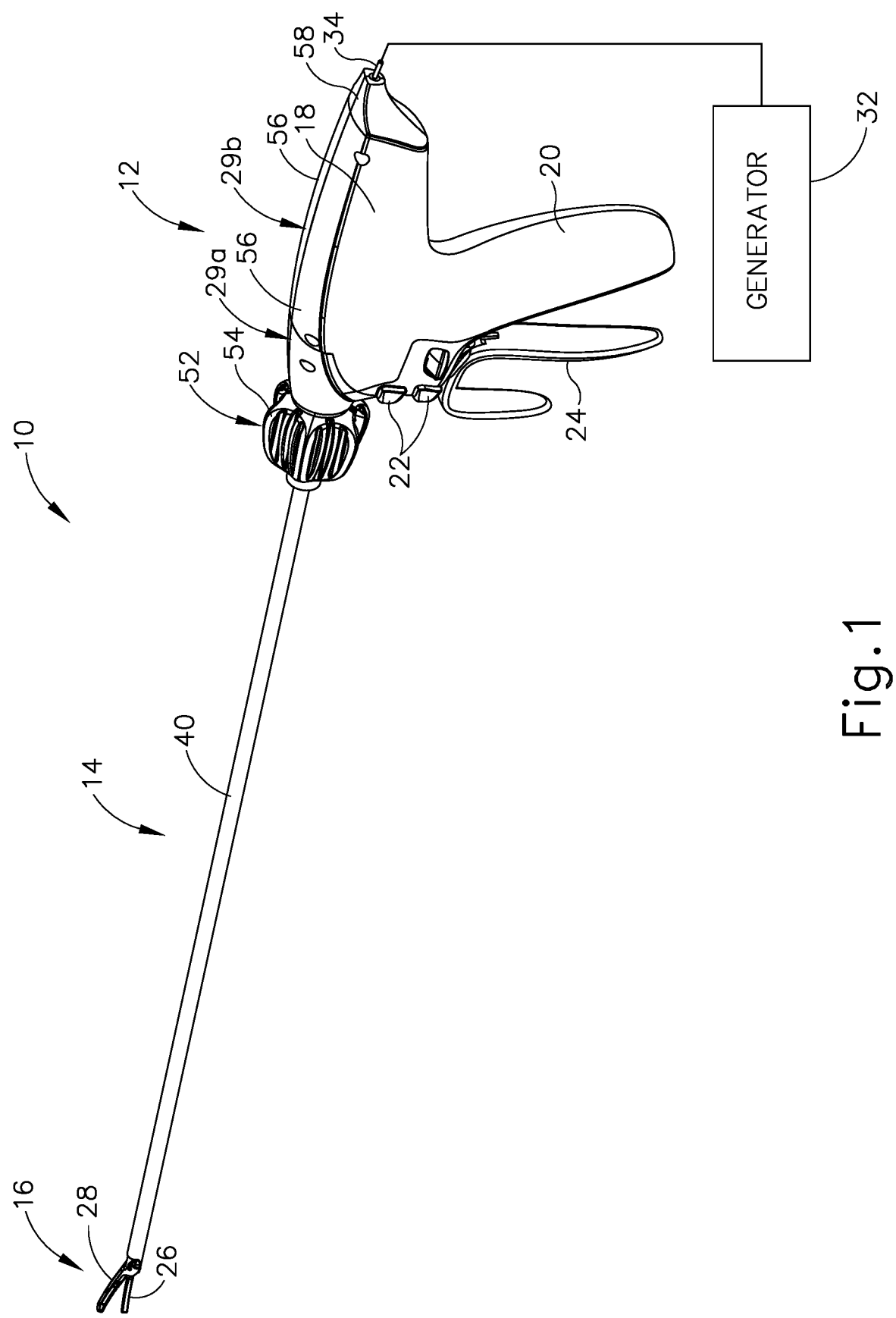
FIG. 1 depicts a perspective view of a first exemplary ultrasonic surgical instrument having a handle assembly, a shaft assembly, and an end effector.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that for convenience and clarity, spatial terms such as "upper," "lower," "inner," and "outer" are used herein with respect to the drawings. However, surgical instruments are used in many orientations and positions, and these terms are not intended to be limiting and absolute. The terms "proximal," "distal," "upper," "lower," "inner," and "outer" are thus relative terms and not intended to unnecessarily limit the invention described herein.

I. Exemplary Ultrasonic Surgical Instrument

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously.

Instrument (10) of the present example comprises a handle assembly (12), a shaft assembly (14), and an end effector (16). Handle assembly (12) comprises a body (18) including a pistol grip (20) and a pair of buttons (22). Handle assembly (12) also includes a trigger (24) that is pivotable toward and away from pistol grip (20). It should be understood, however, that various other suitable configurations may be used, including but not limited to a scissor grip configuration. End effector (16) includes an ultrasonic blade (26) and a pivoting clamp arm (28). Clamp arm (28) is coupled with trigger (24) such that clamp arm (28) is pivotable toward ultrasonic blade (26) in response to pivoting of trigger (24) toward pistol grip (20); and such that clamp arm (28) is pivotable away from ultrasonic blade (26) in response to pivoting of trigger (24) away from pistol grip (20). Various suitable ways in which clamp arm (28) may be coupled with trigger (24) will be apparent to those of ordinary skill in the art in view of the teachings herein. In some versions, one or more resilient members are used to bias clamp arm (28) and/or trigger (24) to the open position shown in FIG. 1.

Figure 2:
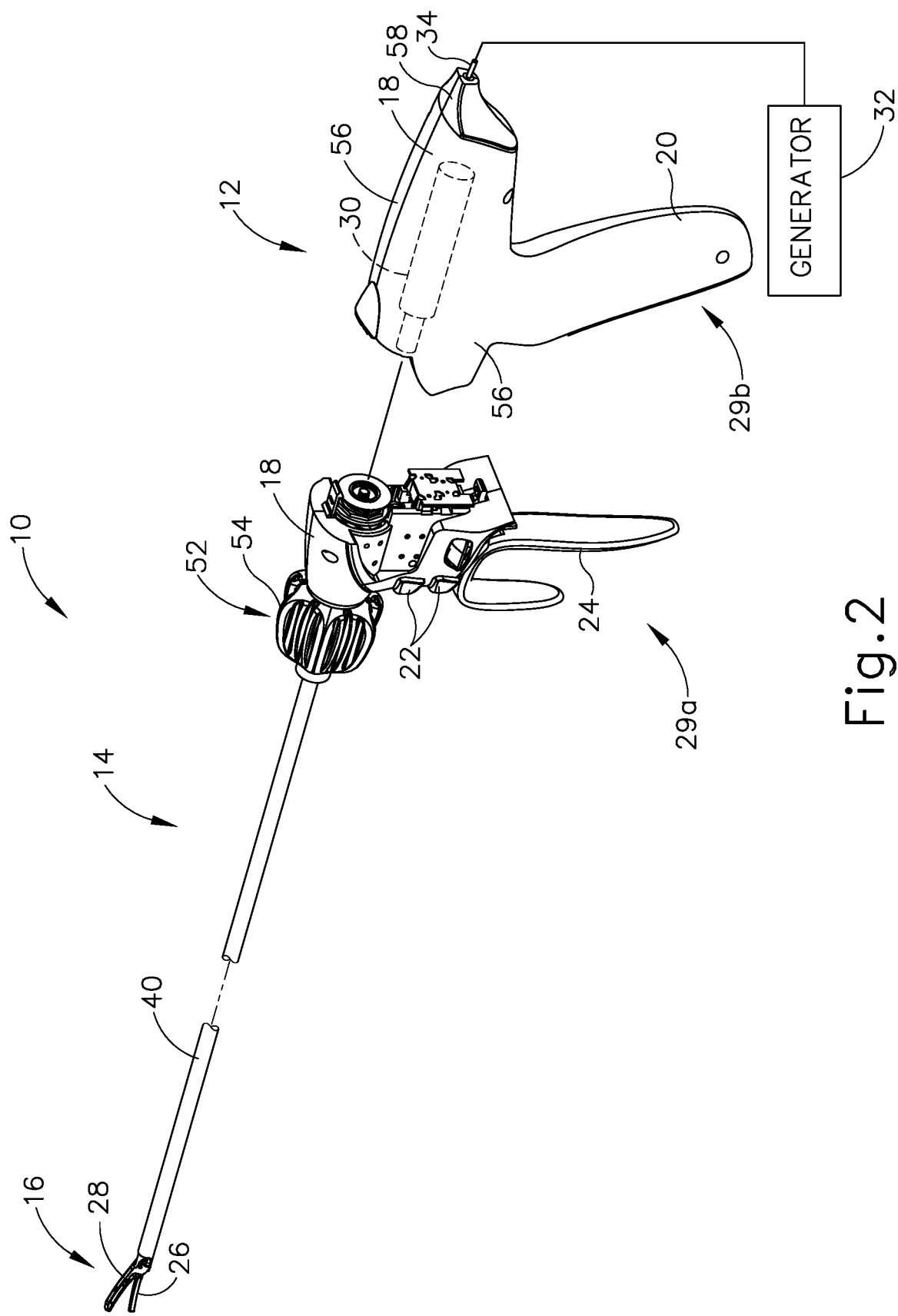
FIG. 2 depicts a partially exploded view of the ultrasonic surgical instrument of FIG. 1 with a disposable portion of the ultrasonic surgical instrument removed from a reusable portion of the ultrasonic surgical instrument.

Furthermore, instrument (10) of this example comprises a disposable assembly (29a) and a reusable assembly (29b) as illustrated in FIG. 2 in more detail. By way of example, disposable assembly (29a) generally includes shaft assembly (14), end effector (16), buttons (22), trigger (24), and a portion of body (18). By way of further example, reusable assembly (29b) generally includes the remaining portion of body (18) with pistol grip (20) and an ultrasonic transducer assembly (30) (see FIG. 5). The distal portion of reusable assembly (29b) is configured to removably receive the proximal portion of disposable assembly (29a), as seen in FIGS. 1-2, to form instrument (10). To accommodate such disposable and reusable assemblies (29a, 29b), shaft assembly (14) and ultrasonic transducer assembly (30) (see FIG. 5) are configured to removably couple together as will be discussed below in greater detail.

Ultrasonic transducer assembly (30) is positioned within body (18) of handle assembly (12). Transducer assembly (30) is coupled with a generator (32) via a cable (34), such that transducer assembly (30) receives electrical power from generator (32) via cable (34). Piezoelectric elements in transducer assembly (30) convert electrical power from generator (32) into ultrasonic vibrations. Generator (32) may include a power source and control module that is configured to provide a power profile to transducer assembly (30) that is particularly suited for the generation of ultrasonic vibrations through transducer assembly (30). By way of example only, generator (32) may comprise a GEN04 or GEN11 sold by Ethicon Endo-Surgery, Inc. of Cincinnati, Ohio. In addition, or in the alternative, generator (32) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (32) may be integrated into handle assembly (12), and that handle assembly (12) may even include a battery or other on-board power source such that cable (34) is omitted, while other cables may alternatively be used for electrically coupling various components. Still other suitable forms that generator (32) may take, as well as various features and operabilities that generator (32) may provide, will be apparent to those of ordinary skill in the art in view of the teachings herein.

In an exemplary use, assemblies (29a, 29b) are coupled together to form instrument (10) and then is used to perform the surgical procedure. Assemblies (29a, 29b) are then decoupled from each other for further processing. In some instances, after the surgical procedure is complete, disposable assembly (29a) is immediately disposed of while reusable assembly (29b) is sterilized and otherwise processed for re-use. By way of example only, reusable assembly (29b) may be sterilized in a conventional relatively low temperature, relatively low pressure, hydrogen peroxide sterilization process. Alternatively, reusable assembly (29b) may be sterilized using any other suitable systems and techniques. In some versions, reusable assembly (29b) may be sterilized and reused approximately 100 times. Alternatively, reusable assembly (29b) may be subject to any other suitable life cycle. For instance, reusable assembly (29b) may be disposed of after a single use, if desired. While disposable assembly (29a) is referred to herein as being "disposable," it should be understood that, in some instances, disposable assembly (29a) may also be sterilized and otherwise processed for re-use. By way of example only, disposable assembly (29a) may be sterilized and reused approximately 2-30 times, using any suitable systems and techniques. Alternatively, disposable assembly (29a) may be subject to any other suitable life cycle.

In some versions, disposable assembly (29a) and/or reusable assembly (29b) includes one or more features that are operable to track usage of the corresponding assembly (29a, 29b), and selectively restrict operability of the corresponding assembly (29a, 29b) based on use. For instance, disposable assembly (29a) and/or reusable assembly (29b) may include one or more counting sensors and a control logic (e.g., microprocessor, etc.) that is in communication with the counting sensor(s). The counting sensor(s) may be able to detect the number of times instrument (10) is activated, the number of surgical procedures the corresponding assembly (29a, 29b) is used in, and/or any other suitable conditions associated with use. The control logic may track data from the counting sensor(s) and compare the data to one or more threshold values. When the control logic determines that one or more threshold values have been exceeded, the control logic may execute a control algorithm to disable operability of one or more components in the corresponding assembly (29a, 29b). In instances where the control logic stores two or more threshold values (e.g., a first threshold for number of activations and a second threshold for number of surgical procedures, etc.), the control logic may disable operability of one or more components in the corresponding assembly (29a, 29b) the first time one of those thresholds is exceeded, or on some other basis.

In versions where a control logic is operable to disable instrument (10) based on the amount of use, the control logic may also determine whether instrument (10) is currently being used in a surgical procedure, and refrain from disabling instrument (10) until that particular surgical procedure is complete. In other words, the control logic may allow the operator to complete the current surgical procedure but prevent instrument (10) from being used in a subsequent surgical procedure. Various suitable forms that counters or other sensors may take will be apparent to those of ordinary skill in the art in view of the teachings herein. Various suitable forms that a control logic may take will also be apparent to those of ordinary skill in the art in view of the teachings herein. Similarly, various suitable control algorithms that may be used to restrict usage of instrument (10) will be apparent to those of ordinary skill in the art in view of the teachings herein. Of course, some versions of instrument (10) may simply omit features that track and/or restrict the amount of usage of instrument (10). Additional and/or alternative features with respect to alternative disposable and reusable assemblies (29a, 29b) may be constructed in accordance with at least some of the teachings of U.S. Pub. No. 2016/0015419, entitled "Ultrasonic Surgical Instrument with Removable Handle Assembly," published Jan. 21, 2016, issued as U.S. Pat. No. 10,349,967 on Jul. 16, 2019, the disclosure of which is incorporated by reference herein. In any case the invention described herein is not intended to be limited to use with only replaceable or reusable components as described herein.

A. Exemplary End Effector and Shaft Assembly

Figure 3A:
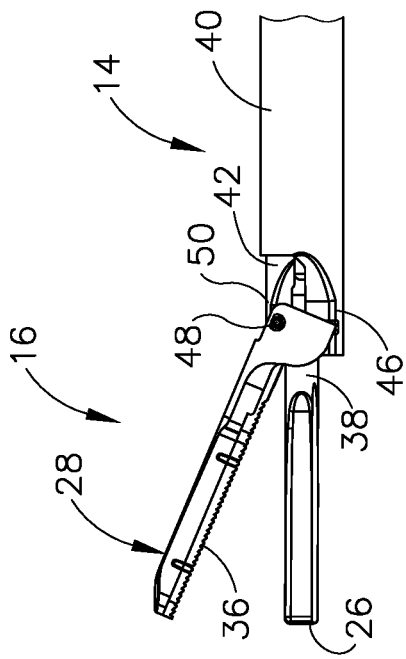
FIG. 3A depicts an enlarged side elevational view of the end effector of FIG. 1 in a closed position.
Figure 3B:
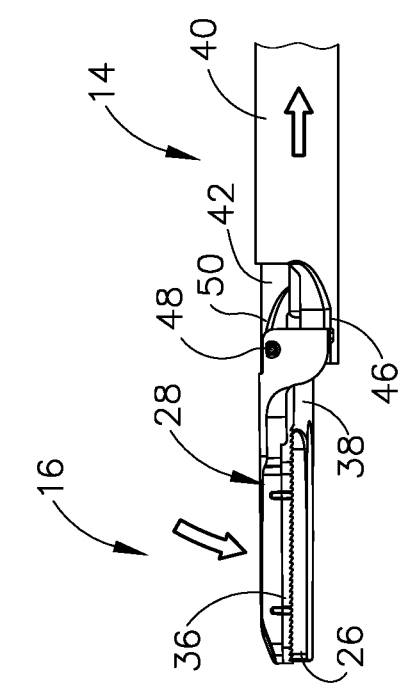
FIG. 3B depicts an enlarged side elevational view of the end effector of FIG. 1 in an open position.

As best seen in FIGS. 3A-3B, end effector (16) of this example comprises clamp arm (28) and ultrasonic blade (26) as discussed briefly above. Clamp arm (28) includes a clamp pad (36), which faces blade (26). Clamp arm (28) is pivotable toward and away from blade (26) to selectively compress tissue between clamp pad (36) and blade (26). More particularly, blade (26) is an integral feature of a distal end of an acoustic waveguide (38), which extends coaxially through tubes (40, 42), and which is configured to communicate ultrasonic vibrations to blade (26) as will be described in greater detail below.

Shaft assembly (14) comprises an outer tube (40) and an inner tube (42). Outer tube (40) is operable to translate longitudinally relative to inner tube (42) to selectively pivot clamp arm (28) toward and away from blade (26). To accomplish this, integral pin features (not shown) extending inwardly from respective projections (44) of clamp arm (28) pivotally secure a first portion of clamp arm (28) to a distally projecting tongue (46) of outer tube (40); while an inserted pin (48) pivotally secures a second portion of clamp arm (28) to a distally projecting tongue (50) of inner tube (42). Thus, tubes (40, 42) cooperate to pivot clamp arm (28) toward blade (26) when outer tube (40) is retracted proximally relative to inner tube (42). It should be understood that clamp arm (28) may be pivoted back away from blade (26) by translating outer tube (40) distally relative to inner tube (42). In an exemplary use, clamp arm (28) may be pivoted toward blade (26) to grasp, compress, seal, and sever tissue captured between clamp pad (36) and blade (26) as shown in FIG. 3A. Clamp arm (28) may also be pivoted away from blade (26), as shown in FIG. 3B, to release tissue from between clamp pad (36) and blade (26); and/or to perform blunt dissection of tissue engaging opposing outer surfaces of clamp arm (28) and blade (26). In some alternative versions, inner tube (42) translates while outer tube (40) remains stationary to provide pivotal movement of clamp arm (28).

As shown in FIGS. 1-2, shaft assembly (14) of the present example extends distally from handle assembly (12). A rotation control assembly (52) has a rotation control member in the form of rotation control knob (54), which is secured to a proximal portion of outer tube (40). Knob (54) is rotatable relative to body (18), such that shaft assembly (14) is rotatable about the longitudinal axis defined by outer tube (40), relative to handle assembly (12). Such rotation may provide rotation of end effector (16) and shaft assembly (30) unitarily, which also includes unitary rotation of acoustic waveguide (38) coupled with transducer assembly (30) within handle assembly (12). In some other versions, various rotatable features may simply be omitted and/or replaced with alternative rotatable features, if desired.

While the present shaft assembly (14) is generally rigid and linear, it will be appreciated that alternative shaft assemblies may include an articulation section (not shown) for deflecting end effector (16) at various lateral deflection angles relative to a longitudinal axis defined by outer tube (40). It will be appreciated that such an articulation section may take a variety of forms. By way of example only, such an articulation section may be configured in accordance with one or more teachings of U.S. Pub. No. 2012/0078247, entitled "Articulation Joint Features for Articulating Surgical Device," published on Mar. 29, 2012, issued as U.S. Pat. No. 9,402,682 on Aug. 2, 2016, the disclosure of which is incorporated by reference herein. As another merely illustrative example, an articulation section may be configured in accordance with one or more teachings of U.S. Pub. No. 2014/0005701, issued as U.S. Pat. No. 9,393,037 on Jul. 19, 2016 and/or U.S. Pub. No. 2014/0114334, issued as U.S. Pat. No. 9,095,367 on Aug. 4, 2015, the disclosures of which are incorporated by reference herein. Various other suitable forms that an articulation section may take will be apparent to those of ordinary skill in the art in view of the teachings herein.

B. Exemplary Handle Assembly

As seen in FIGS. 1 and 2, handle assembly (12) is reusable as discussed above and comprises body (18) defined by a pair of complementary housings (56) joined together. Housings (56) collectively define pistol grip (20) and include a cord support base (58) through which cable (34) extends between transducer assembly (30) and generator (32). While body (18) includes pistol grip (20) in this example, it should be understood that any other suitable kind of grip may be used.

Waveguide (38) extends proximally through knob (54) and into body (18) to mechanically couple with transducer assembly (30). When waveguide (38) is sufficiently coupled with transducer assembly (30), ultrasonic vibrations that are generated by transducer assembly (30) are communicated along waveguide (38) to reach blade (26). In the present example, the distal end of blade (26) is located at a position corresponding to an anti-node associated with resonant ultrasonic vibrations communicated through waveguide (38), in order to tune the acoustic assembly to a preferred resonant frequency $f_o$ when the acoustic assembly is not loaded by tissue. When transducer assembly (30) is energized, the distal end of blade (26) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (30) of the present example is activated, these mechanical oscillations are transmitted through waveguide (38) to reach blade (26), thereby providing oscillation of blade (26) at the resonant ultrasonic frequency. Thus, when tissue is secured between blade (26) and clamp pad (36), the ultrasonic oscillation of blade (26) may simultaneously sever the tissue and denature the proteins in adjacent tissue cells, thereby providing a coagulative effect with relatively little thermal spread. In some versions, an electrical current may also be provided through blade (26) and/or clamp pad (36) to also seal the tissue.

Further exemplary features and operabilities for disposable and/or reusable portions of surgical instrument (10) will be described in greater detail below, while other variations will be apparent to those of ordinary skill in the art in view of the teachings.

C. Exemplary Torque Wrench

Figure 4:
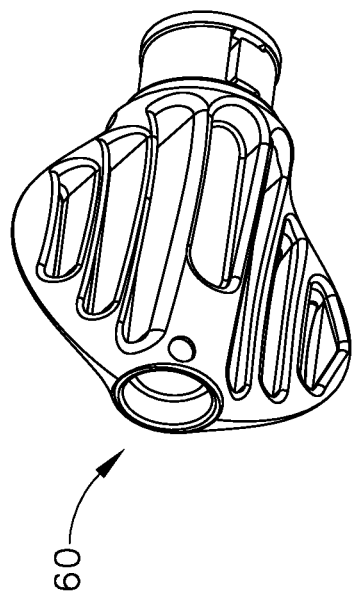
FIG. 4 depicts a perspective view of a torque wrench for coupling the shaft assembly of FIG. 1 to the handle assembly of FIG. 1.

In the present example, waveguide (38) is threadably secured to transducer assembly (30) for acoustically coupling waveguide (38) with transducer assembly (30) for use. In order to properly communicate the resonant ultrasonic vibrations from transducer assembly (30) to waveguide (38), a predetermined torque is applied to waveguide (38) during installation with transducer assembly (30). As seen in FIG. 4, a separate torque wrench (60) is used to couple the waveguide (38) with the transducer assembly (30) to inhibit overtightening of the waveguide (38). It should be understood that torque wrench (60) may ensure that a sufficient level of torque is used to couple waveguide (38) with transducer assembly (30) (i.e., to avoid separation of waveguide (38) from transducer assembly (30) while waveguide (38) and transducer assembly (30) are ultrasonically activated); while also preventing too much torque from being used to couple waveguide (38) with transducer assembly (30) (i.e., to avoid undue stress and the risk of breakage at the coupling of waveguide (38) from transducer assembly (30) while waveguide (38) and transducer assembly (30) are ultrasonically activated).

Torque wrench (60) of the present example may be slid proximally along shaft assembly (14) until torque wrench (60) engages knob (54), such that rotating torque wrench (60) similarly rotates knob (54), thereby rotating shaft assembly (14). During installation, a proximal end portion of waveguide (38) is received within a threaded hole (not shown) of transducer assembly (30). The operator rotates shaft assembly (14) via torque wrench (60), while holding handle assembly (12) stationary, thereby rotating waveguide (38) relative to transducer assembly (30). The proximal end portion of waveguide (38) is thus rotated into threaded engagement with transducer assembly (30). As installation torque increases during rotation, torque wrench (60) is configured to slip relative to knob (54) once the applied torque being transmitted therethrough exceeds the predetermined torque. In addition to slipping, torque wrench (60) generates audible and tactile "clicks" once the predetermined torque is achieved. Torque wrench (60) thus inhibits overtightening of waveguide (38) to transducer assembly (30). By way of further example only, torque wrench (60) may be configured and operable in accordance with at least some of the teachings of U.S. Pub. No. 2007/0191713, entitled "Ultrasonic Device for Cutting and Coagulating," published Aug. 16, 2007, now abandoned, the disclosure of which is incorporated by reference herein.

II. Handle Assembly with Integral Torque Wrench for Coupling Waveguide with Transducer Assembly As described above with respect to surgical instrument (10), once waveguide (38) and transducer assembly (30) are secured together at the predetermined torque, selective rotation of knob (54) collectively rotates the remainder of shaft assembly (14), end effector (16), waveguide (38), and transducer assembly (30) relative to handle assembly (12). However, even before proper installation at the predetermined torque, the proximal end of waveguide (38) may have enough frictional engagement with transducer assembly (30) to cause transducer assembly (30) to rotate with waveguide (38) relative to handle assembly (12). Such engagement may make it difficult, or even impossible in some cases, for a user to apply the predetermined torque for proper coupling of the waveguide (38) to transducer assembly (30), because the user may not be able to apply a reactionary torque to transducer assembly (30) up to the predetermined torque.

In order to facilitate coupling of waveguide (38) with transducer assembly (30), some versions of surgical instrument (10) may include a transducer lock. Various exemplary transducer locks are described in greater detail in U.S. patent application Ser. No. 15/378,432, entitled "Ultrasonic Surgical Instrument with Integral Shaft Assembly Torque Wrench," filed on Dec. 14, 2016, published as U.S. Pub. No. 2018/0161059 on Jun. 14, 2018, the disclosure of which is incorporated by reference herein; U.S. patent application Ser. No. 15/378,452, entitled "Ultrasonic Surgical Instrument with Transducer Locking Feature," filed on Dec. 14, 2016, published as U.S. Pub. No. 2018/0161060 on Jun. 14, 2018, the disclosure of which is incorporated by reference herein; and U.S. patent application Ser. No. 15/378,414, entitled "Ultrasonic Surgical Instrument with Integral Torque Wrench and Transverse Engagement," filed on Dec. 14, 2016, published as U.S. Pub. No. 2018/0161058 on Jun. 14, 2018, the disclosure of which is incorporated by reference herein.

While a transducer lock may inhibit rotation of transducer assembly (30), the separate torque wrench (60) is applied to shaft assembly (14) in at least some of the above referenced examples for providing the predetermined torque while inhibiting overtightening of waveguide (38) with transducer assembly (30). However, handling and manipulating torque wrench (60) separately from surgical instrument (10) may add further complexity to the surgical procedure and may be difficult to manage in some instances. Moreover, torque wrench (60) may wear out over a number of uses and maintaining the torque wrench (60) to provide clear and accurate limitations on torque to the predetermined torque may also be difficult over time. It may thus be desirable to integrate a torque wrench, or at least some of the features and operability of torque wrench (60), into handle assembly (12) of surgical instrument (10) in order to provide both torque limiting and transducer assembly seizing features.

The following description relates to various exemplary torque wrenches (110, 210, 310) integrated into surgical instruments (112, 212, 312) discussed below in greater detail. Accordingly, like numbers described herein indicate like features with respect to each exemplary torque wrench (110, 210, 310). While torque wrenches (110, 210, 310) are configured to selectively inhibit, and even prevent rotation of transducer assembly (30) relative to body (18), in addition to limiting torque, it will be appreciated that some rotation in alternative examples is possible in accordance with the invention. For example, alternative torque wrenches may not strictly prevent rotation, but at least inhibit rotation enough to provide a reactionary torque equal to at least the predetermined torque for proper installation. The invention is thus not intended to be unnecessarily limited to preventing all relative rotation between transducer assembly (30) and body (18).

A. Exemplary Proximal Detent Cam Slip Lock

Figure 5:
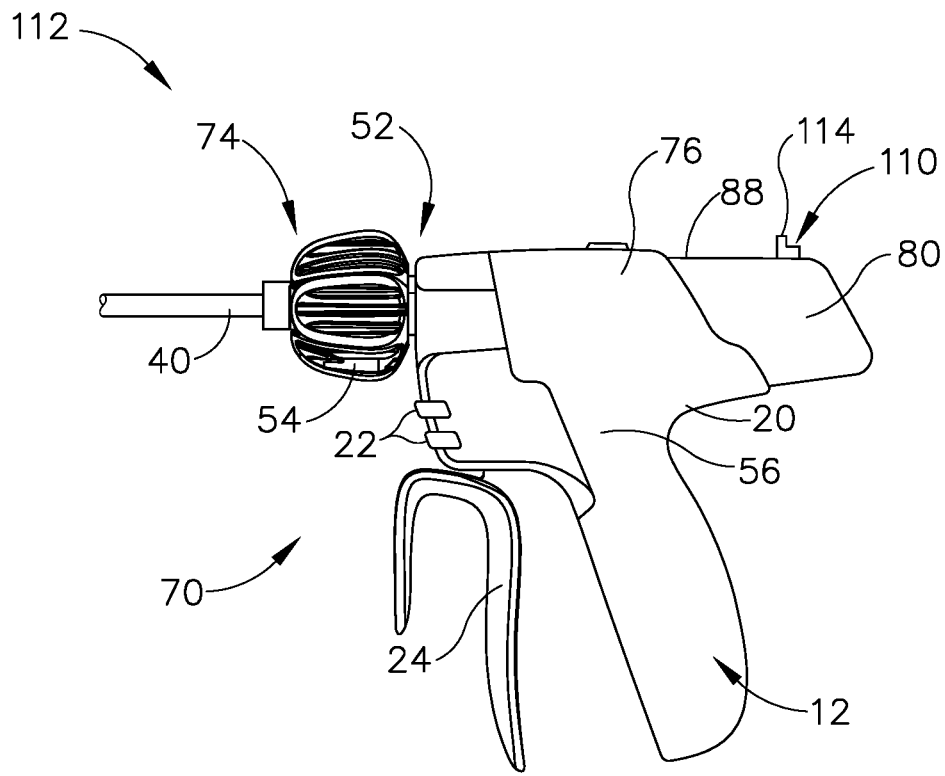
FIG. 5 depicts a side elevational view of a second exemplary ultrasonic surgical instrument with a proximal detent cam slip lock.
Figure 6:
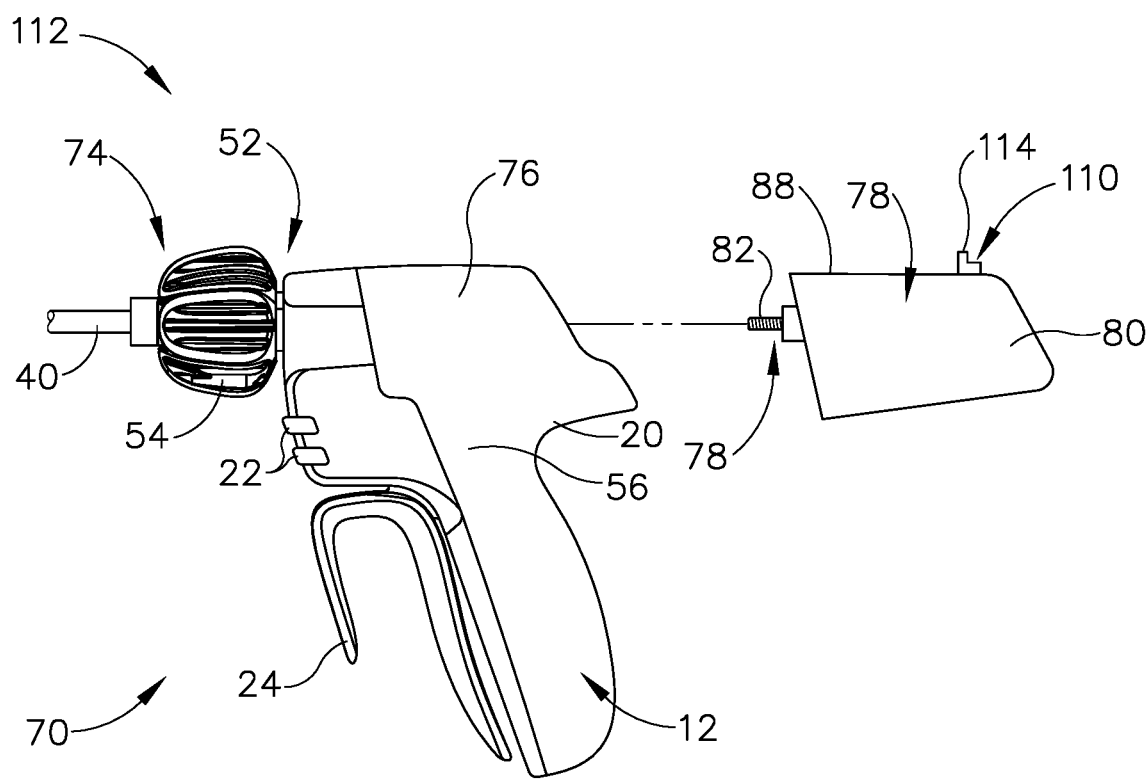
FIG. 6 depicts a partially exploded side elevational view of the ultrasonic surgical instrument of FIG. 5 with a proximal portion of the ultrasonic surgical instrument removed from a remainder of the ultrasonic surgical instrument.
Figure 7:
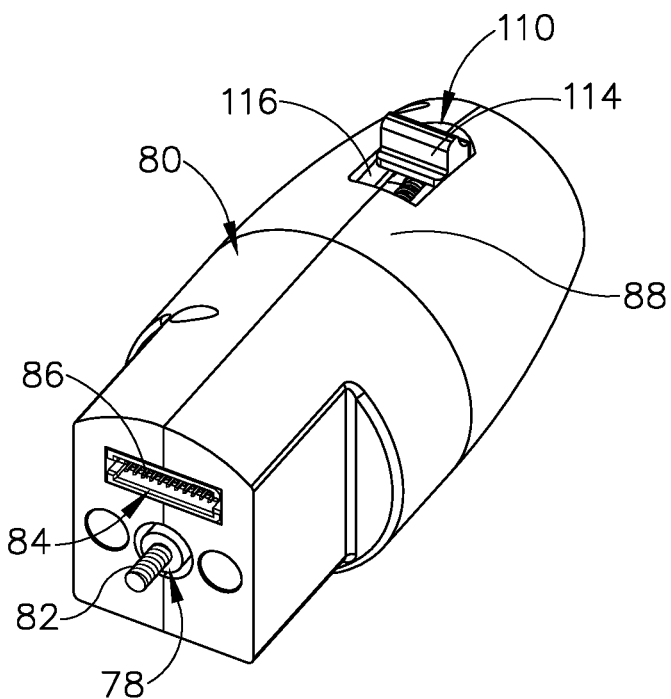
FIG. 7 depicts a distal perspective view of the proximal portion of the ultrasonic surgical instrument with the proximal detent cam slip lock of FIG. 5.

FIGS. 5-16 illustrate a first exemplary torque wrench assembly in the form of a proximal detent cam slip lock (110) of a surgical instrument (112), which is configured to both inhibit rotation of transducer assembly (30) and limit torque applied to waveguide (38) to the predetermined torque. As seen in FIGS. 5-7, surgical instrument (112) includes a distal portion (70) and a proximal portion (72). Distal portion (70) has a shaft assembly (74) with knob (54) and waveguide (38) (see FIG. 2), end effector (16) (see FIG. 2), buttons (22), trigger (24), and a portion of a body (76), at least a portion of which may also be referred to as shaft assembly body (76). Proximal portion (72) generally includes pistol grip (20) and a transducer assembly (78) contained within a cover (80) for storage and protection. Accordingly, cover (80) may also be considered a remaining portion of body (76) of surgical instrument (112). One or both of distal and proximal portions (70, 72) of surgical instrument (112) may be disposable and/or reusable as discussed above with respect to surgical instrument (10) (see FIG. 1).

FIGS. 6-7 illustrate proximal portion (72) in greater detail. In the present example, a proximal end portion of waveguide (38) (see FIG. 2) has a threaded hole (not shown) coaxially positioned therein, whereas transducer assembly (78) has a threaded stud (82) configured to be threadably received within threaded hole (not shown) for coupling. In addition, proximal portion (72) also includes slip lock (110) as discussed below in greater detail. Above a portion of transducer assembly (78) within cover (80), a circuit board (84) and electrical connector (86) are configured to electrically connect to distal portion (70) for electrical communication therebetween during the surgical procedure.

Figure 8:
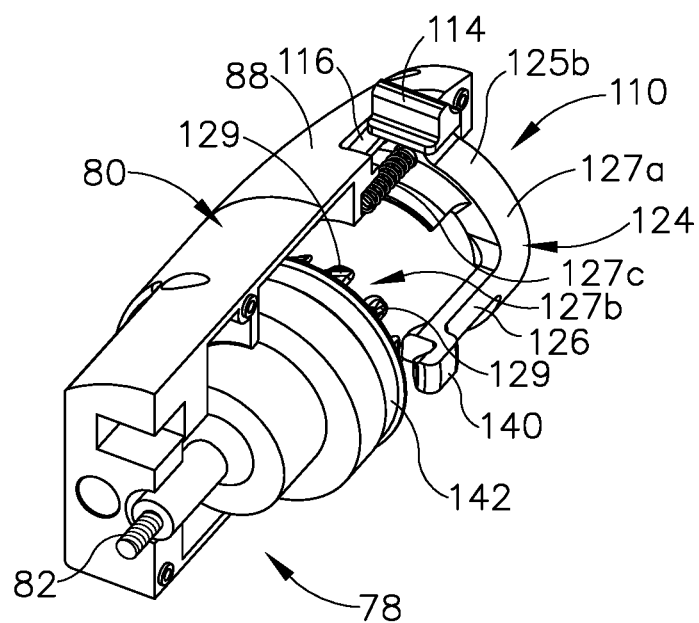
FIG. 8 depicts a distal perspective view of the proximal portion of the ultrasonic surgical instrument with the proximal detent cam slip lock of FIG. 5, with various components removed for more clearly showing an ultrasonic transducer assembly and the proximal detent cam slip lock in an unlocked position.

As shown in FIG. 8, slip lock (110) includes a lock switch (114) extending through a lock channel (116) in cover (80). More particularly, lock channel (116) extends longitudinally and transversely through an upper surface (88) of cover (80) directly above the longitudinal axis. Lock switch (114) is thus translatable between an upper, unlocked position and a lower, locked position for respectively unlocking and locking rotation of transducer assembly (78) relative to cover (88) and distal portion (70) of surgical instrument (112). While lock switch (114) and lock channel (116) are positioned on upper surface (88) of body (80) of the present example, it will be appreciated that lock switch (114) and lock channel (116) may be alternatively positioned so as to cooperate with transducer assembly (78). The invention is thus not intended to be unnecessarily limited to having lock switch (114) and lock channel (116) positioned as shown herein.

FIG. 8 more particularly illustrates lock switch (114) in a proximal, unlocked position and configured to longitudinally translate in a distal direction to a distal, locked position. While not shown with respect to the present example of slip lock (110), it will be appreciated that upper surface (88), or another portion of surgical instrument (112) may further include an unlocked indicia (not shown) and/or a locked indicia (not shown) for visually indicating a rotational state (i.e., unlocked state or locked state) of transducer assembly (78) to the user.

Figure 9:
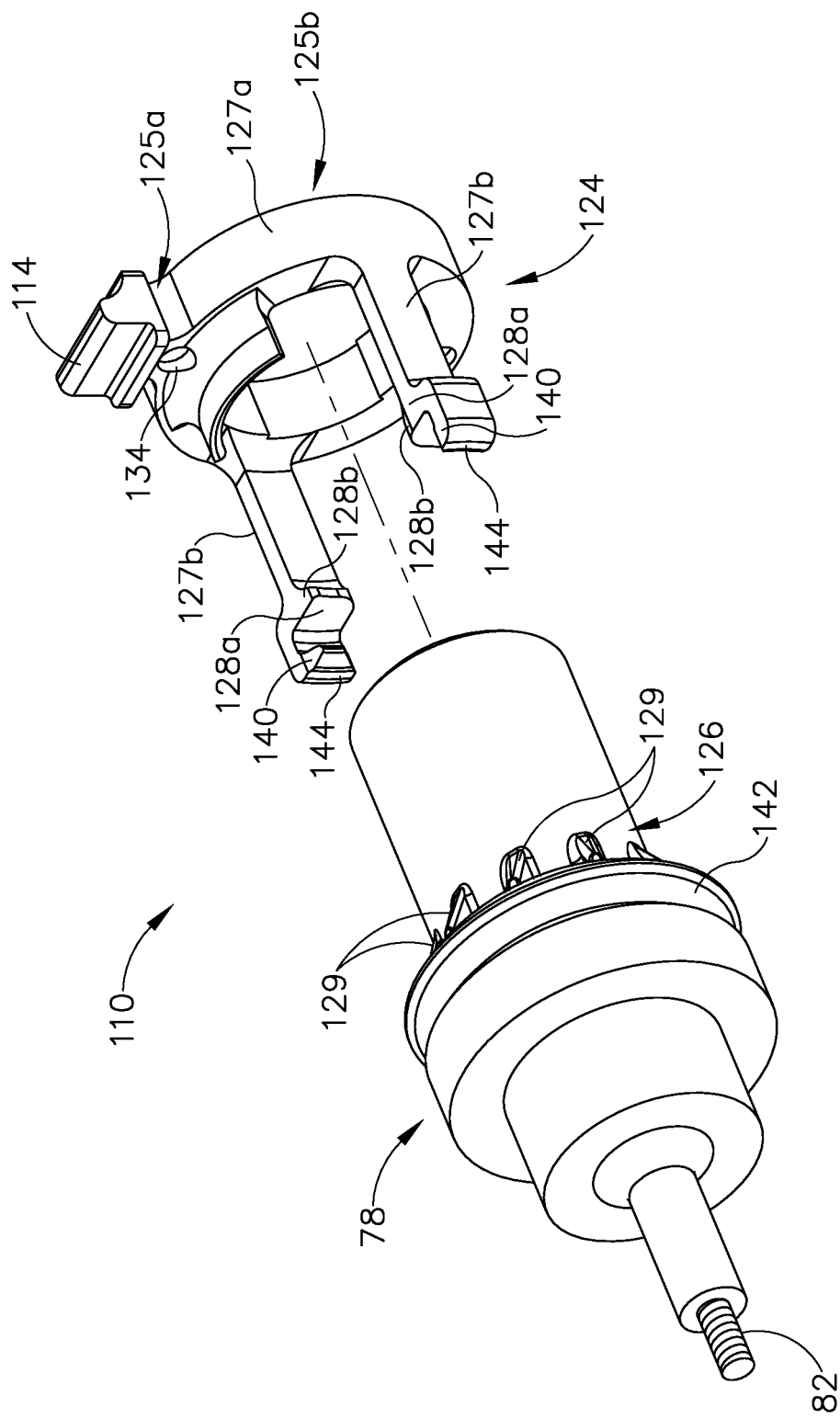
FIG. 9 depicts a partially exploded distal perspective view of the proximal detent cam slip lock and the ultrasonic transducer assembly of FIG. 8.

As seen in FIGS. 8-10, slip lock (110) further includes an arrester (124) that is operatively connected to lock switch (114) and an engagement feature (126) that is operatively connected to transducer assembly (78). Arrester (124) and engagement feature (126) are configured to cooperate with each other to selectively allow or inhibit rotation of transducer assembly (78) relative to cover (80). Arrester (124) of the present example extends transversely downwardly from lock switch (114) about the longitudinal axis and, in the unlocked position, is proximally offset from engagement feature (126). More particularly, arrester (124) includes a downward stem (125a) extending transversely downwardly from lock switch (114) to an arrester body (125b), which also extends transversely downwardly from stem (125a).

Arrester body (125b) of the present example generally has a deflectable portion and a catch portion and more particularly includes an annular base (127a) surrounding a proximal portion of transducer assembly (78) and a pair of resilient catch arms (127b) extending longitudinally and distally therefrom toward engagement feature (126). Each catch arm (127b) collectively defines the deflectable portion and has the catch portion extending therefrom in the present example. Catch arms (127b) respectively include a pair of catch cams (128a) with catch surfaces (128b) that are configured to longitudinally engage engagement feature (126) for seizing transducer assembly (78). As will be described below in greater detail, catch arms (127b) are configured to deflect relative to engagement feature (126) upon application of torque to transducer assembly (30) greater than the predetermined torque upon installation of waveguide (38). In addition, while also limiting torque applied between waveguide (38) and transducer assembly (30), catch arms (127b) also secure catch surface (128b) and lock switch (114) in the locked position despite being biased by a biasing element (127c) toward the unlocked position as shown FIG. 8. The user may then manipulate other portions of surgical instrument (112) without necessarily holding lock switch (114) in the locked position.

As shown in FIGS. 11-12, engagement feature (126) of the present example is more particularly in the form of a transducer housing, also referred to herein as a transducer can (126), having a plurality of cam teeth (129) radially and rigidly extending outward therefrom. The plurality of cam teeth (129) are positioned angularly about transducer can (126) and, in the present example, include ten equiangularly position teeth (129), although it will be appreciated that an alternative number of such teeth (129) may be so used for engagement with catch surfaces (128b) as shown in FIGS. 12-13B. Each tooth (129) has an angled cam face (130) that intersects transducer can (126) at an obtuse angle. Thus, upon rotation of transducer can (126), each cam face (130) is configured to urge catch surface (128b) of each catch arm (127b) resiliently outwardly from transducer can (126) as will be discussed below in greater detail with respect to FIG. 16 for allowing rotation beyond the predetermined torque.

Figure 13A:
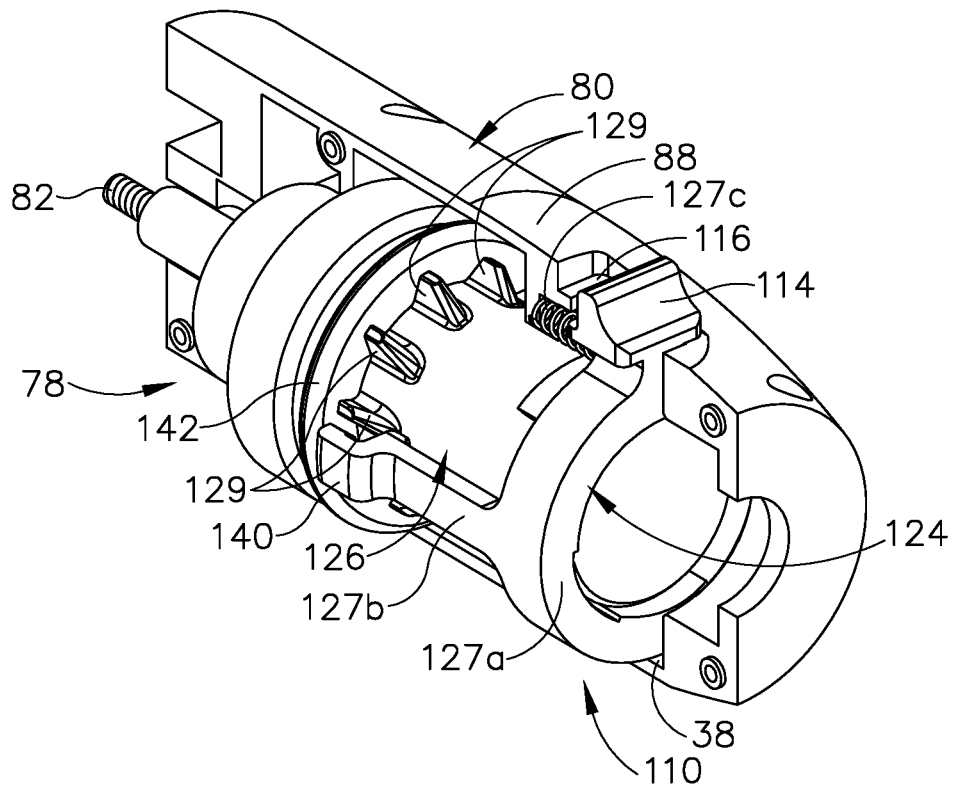
FIG. 13A depicts a proximal perspective view of the proximal portion of the ultrasonic surgical instrument of FIG. 8, with the proximal detent cam slip lock in the unlocked position.
Figure 13B:
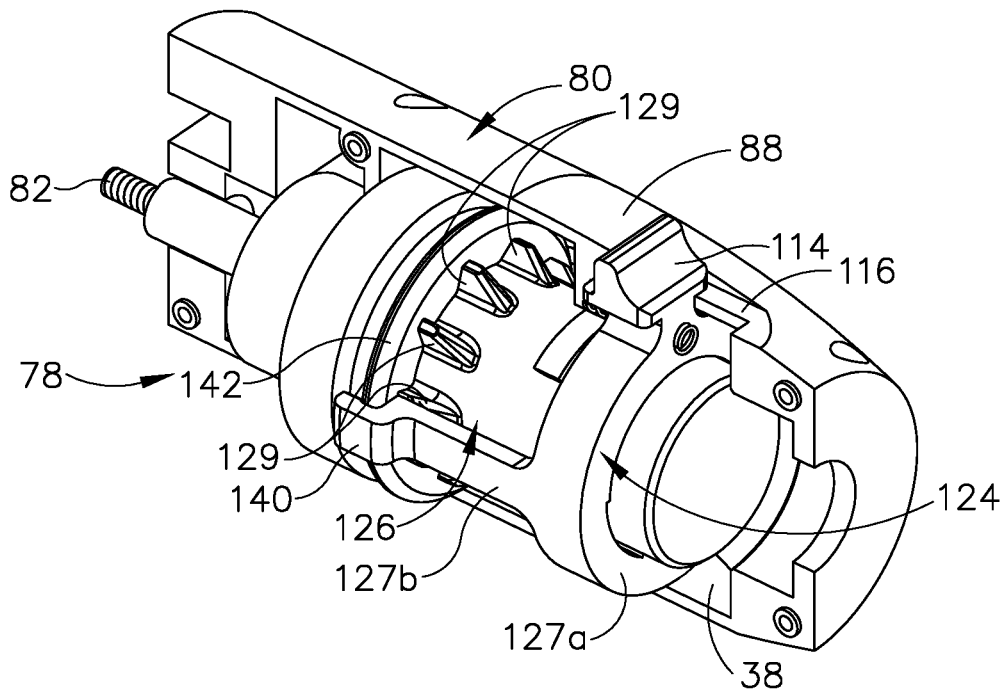
FIG. 13B depicts a proximal perspective view of the proximal portion of the ultrasonic surgical instrument of FIG. 8, with the proximal detent cam slip lock in a locked position.
Figure 14A:
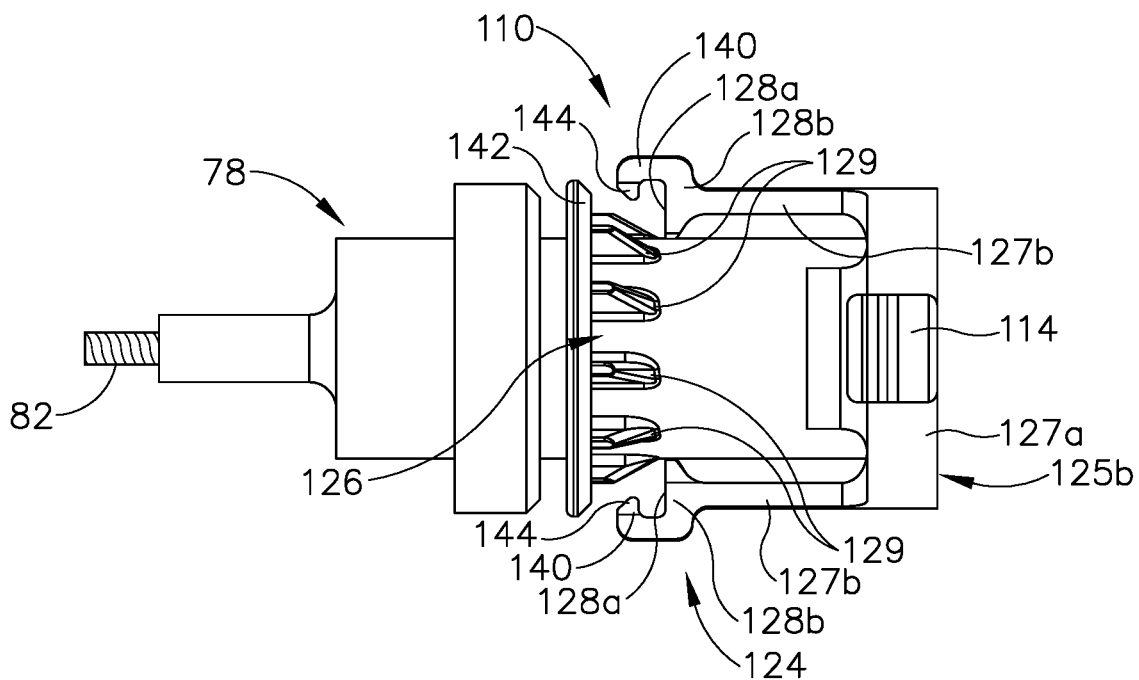
FIG. 14A depicts an upper plan view of the ultrasonic transducer assembly of FIG. 9, with the proximal detent cam slip lock in the unlocked position.
Figure 14B:
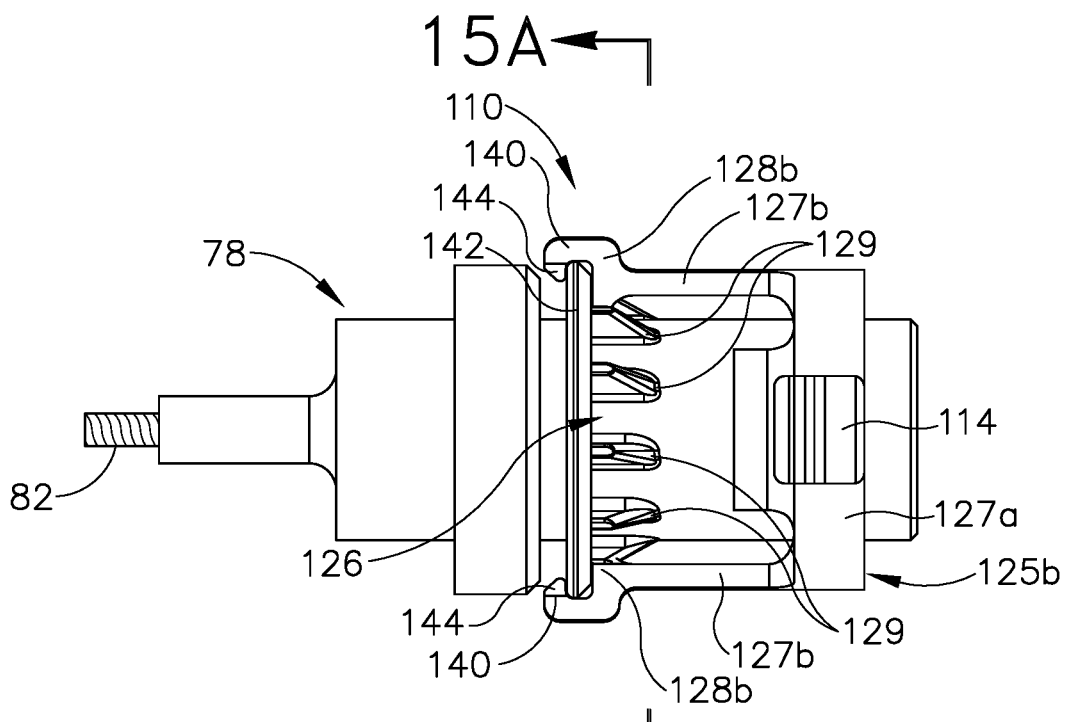
FIG. 14B depicts an upper plan view of the ultrasonic transducer assembly of FIG. 9, with the proximal detent cam slip lock in the locked position.

FIGS. 13A and 14A illustrate arrester (124) and lock switch (114) in the proximal, unlocked position and translatably mounted within cover (80) to be selectively moved to the distal, locked position. As briefly discussed above, arrester (124) is biased proximally toward the disengaged position by biasing element (127c) captured against cover (80). More particularly, downward stem (125a) includes a stem mount (134) longitudinally offset from a cover mount (136), which transversely extends downwardly within cover (80). Biasing element (127c), which is more particularly in the form of a coil spring, is captured in compression between stem and body mounts (134, 136) such that spring (127c) urges stem mount (134) proximally, thereby directing arrester (124) toward the disengaged position and lock switch (114) toward the unlocked position. While arrester (124) may be translated proximally and distally between disengaged and engaged positions via manipulation of lock switch (114) by the user, arrester (124) is movably secured within a gap (138) defined between an outer surface of transducer can (126) and an inner surface of cover (80). Of course, it will be appreciated that alternative structures configured to movably secure arrester (124) within cover (80) may be similarly used. In the proximal, disengaged position shown in FIGS. 13A and 14A, the catch surfaces (128b) of catch cams (128a) are proximally offset from the plurality of cam teeth (129) to permit rotation of transducer assembly (78) relative to arrester (124). However, distally translating catch cams (128a) between and against respective cam teeth (129) tends to inhibit relative rotation as shown in FIGS. 13B and 14B.

Arrester (124) is further configured to secure against transducer assembly (78) while inhibiting rotation up to the predetermined torque and then release transducer assembly (78) upon receiving torque greater than the predetermined torque to allow for relative rotation. To this end, each catch arm (127b) further includes a distally projecting detent latch (140), whereas transducer can (126) has an annular detent latching flange (142) extending radially therefrom. Detent latch (140) longitudinally captures annular detent flange (142) in the engaged position to longitudinally secure arrester (124) relative to transducer assembly (78) and cooperatively align catch cams (128a) with the plurality of cam teeth (129) to inhibit relative rotation. To aid detent latch (140) with capturing annular detent flange (142), detent latch (140) has a distal cam surface (144) that deflects detent latch (140) resiliently outwardly to effectively hook catch arm (127) with the inward return of catch arm (127b) as arrester (124) reaches the engaged position shown in FIG. 15A.

Figure 15A:
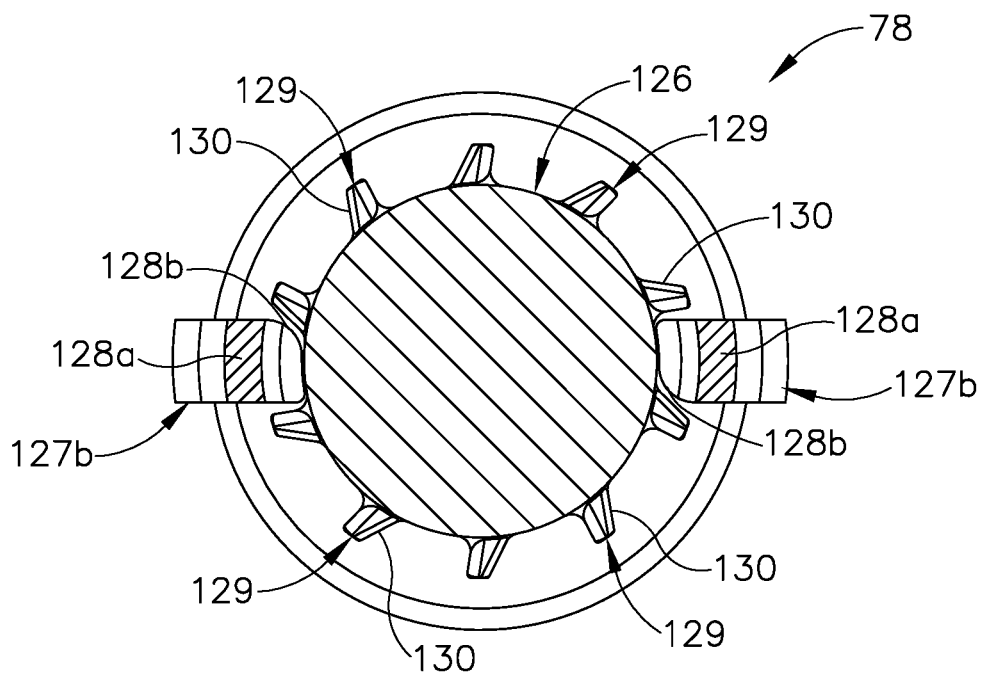
FIG. 15A depicts a cross-sectional view of the ultrasonic transducer assembly of FIG. 14A, taken along section line 15A-15A of FIG. 14B, showing the proximal detent cam slip lock in the locked position.
Figure 15B:
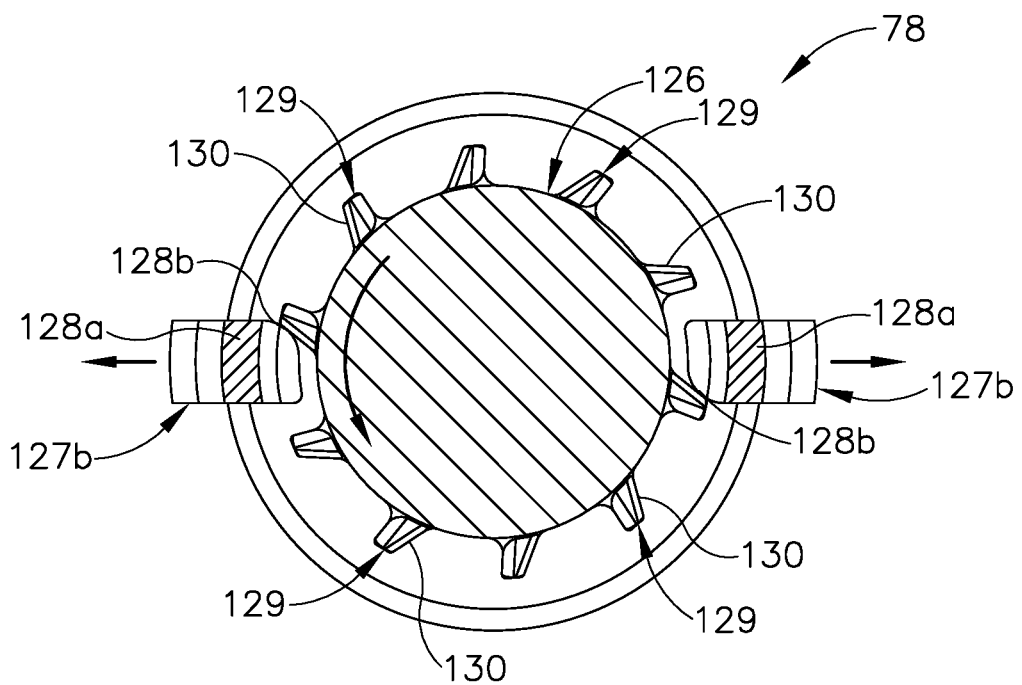
FIG. 15B depicts a cross-sectional view of the ultrasonic transducer assembly of FIG. 14A, taken along section line 15A-15A of FIG. 14B, showing the arrester inhibiting rotation of the engagement collar while also showing a portion of the arrester deflecting to limit coupling torque between an acoustic waveguide the ultrasonic transducer assembly.
Figure 15C:
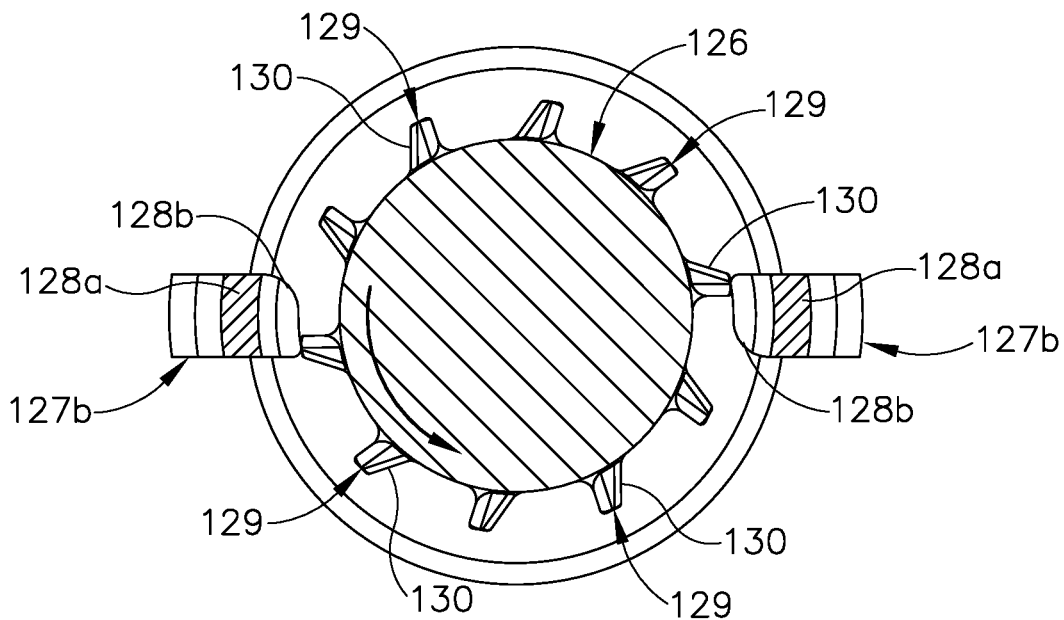
FIG. 15C depicts a cross-sectional view of the ultrasonic transducer assembly of FIG. 14A, taken along section line 15A-15A of FIG. 14B, showing the ultrasonic transducer assembly slipping relative to the arrester.
Figure 16:
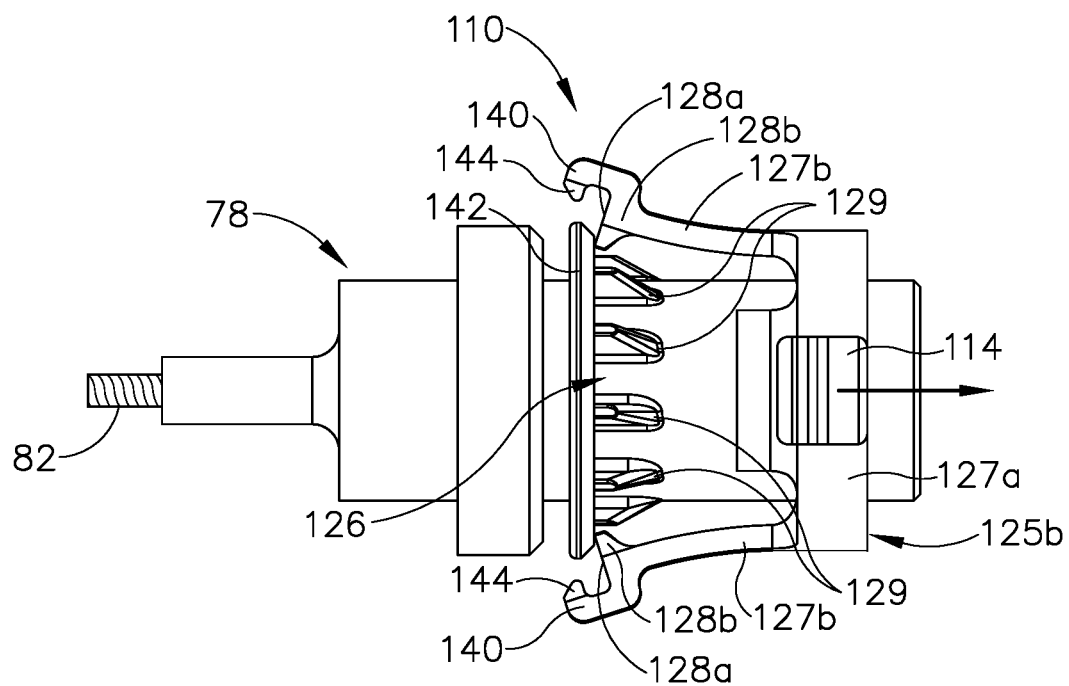
FIG. 16 depicts an upper plan view of the ultrasonic transducer assembly of FIG. 9, with the proximal detent cam slip lock returning from the locked position toward the unlocked position.

FIGS. 15A-15B illustrate catch cams (128a) respectively positioned between pairs of cam teeth (129) and configured to inhibit rotation of transducer assembly (78) relative to arrester (124) up to the predetermined torque with which to threadably connect waveguide (38) (see FIG. 2) to transducer assembly (78). Each catch arm (127b) extends distally from annular base (127a) of arrester body (125b) as a cantilever and is configured to outwardly deflect away from the longitudinal axis as the applied torque exceeds the predetermined torque. Notably, catch arms (127b), catch cams (128a), and the plurality of cam teeth (129) are collectively tuned such that catch cams (128a) deflect outwardly to longitudinally clear cam teeth (129) as the applied torque exceeds the predetermined torque. Each tooth face (130) is configured to effectively urge each catch surface (128b) radially outwardly as shown in FIG. 15B upon the application of such torque. Transducer can (126) with transducer assembly (78) may thus slip relative to catch surfaces (127) to inhibit overtightening waveguide (38) with transducer assembly beyond the predetermined torque with respect to FIG. 15C.

In the present example, catch arms (127b), catch cams (128a) with catch surfaces (128b), and detent latches (140) respectively deflect outwardly together upon the application of such torque to allow for slippage beyond the predetermined torque to inhibit overtightening of waveguide (38) with transducer assembly (78). In the event that alternative and/or additional mechanisms are incorporated into an alternative slip lock, it will be appreciated that similar tuning may be done in accordance with the invention. The invention is thus not intended to be unnecessarily limited to the particular arrangement of transducer can (126), catch arms (127b), catch cams (128a) with catch surfaces (128b), and detent latches (140).

In an exemplary use, shaft assembly (74) is initially uncoupled from transducer assembly (78). The user translates lock switch (114) of slip lock (110) distally from the unlocked position to the locked position such that catch surfaces (128b) of arrester (124) engage cam teeth (129) to seize rotation of transducer assembly (78) relative to cover (80). Simultaneously, detent flange (142) urges distal cam surfaces (144) of detent latches (140) radially outwardly and, in turn, deflects catch arms (127b) radially outwardly so that each detent latch (140) longitudinally clears detent flange (142). As catch arms (127b) of arrester (124) reach the engaged position, each detent latch (140) releasably captures detent flange (142) in the longitudinal direction to inhibit relative longitudinal movement between arrester (124) and transducer assembly (78).

The user then introduces threaded stud (82) of transducer assembly (78) into the proximal end portion of waveguide (38) and rotates knob (54) in a tightening direction to threadably engage the proximal end portion of waveguide (38) with transducer assembly (78). Even as frictional engagement between the waveguide (38) and transducer assembly (78) increases, in turn increasing applied torque, catch cams (128a) of arrester (124) continue to engage respective cam teeth (129) to inhibit rotation of engagement collar (126). The user thus continues to tighten waveguide (38) into transducer assembly (78) until reaching the predetermined torque. As applied torque increases, respective tooth faces (130) urge catch surfaces (128b) of catch cams (128) radially outwardly and, in turn, catch arms (127b) outwardly deflect until reaching the predetermined torque. Once detent latches (140) radially clear detent flange (142), coil spring (127c) urges arrester (124) from the engaged position to the disengaged position, thereby allowing cam teeth (129) to similarly clear catch cams (128a) and freely rotate relative to each other for inhibiting overtightening of waveguide (38) therein.

In some alternative versions, arrester (124) may remain in the engaged position, yet simply allow slippage of transducer assembly (78) beyond the predetermined torque to inhibit overtightening with waveguide (38). In some such versions, the user may then manually manipulate lock switch (114) and arrester (124) to their respective unlocked and disengaged positions as desired. In any case, with waveguide (38) coupled to transducer assembly (30) at the predetermined torque, the user may then collectively rotate waveguide (38) and transducer assembly (78) via knob (54) during the surgical procedure.

By way of further example, slippage of catch cams (128a) relative to cam teeth (129) and the resilient return of catch arms (128b) inwardly to their original position may also generate an audible indicator, a tactile indicator, or other signal to the user that waveguide (38) is coupled with transducer assembly (78) at the predetermined torque. Slip lock (110) may thus also provide an integral torque indicator for indicating to the user that waveguide (38) has been coupled to the transducer assembly (78) with the predetermined torque.

B. Exemplary Distal Detent Cam Slip Lock

Figure 17A:
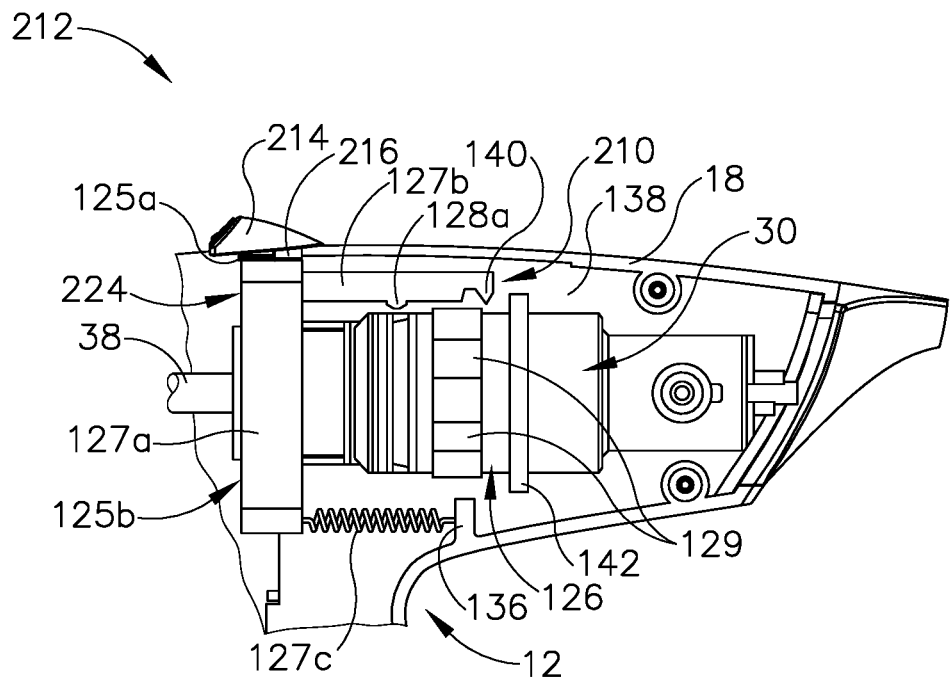
FIG. 17A depicts an enlarged a side elevational view of a third exemplary ultrasonic surgical instrument with a distal detent cam slip lock, but having various components removed for more clearly showing an ultrasonic transducer assembly and the distal detent cam slip lock in an unlocked position.
Figure 17B:
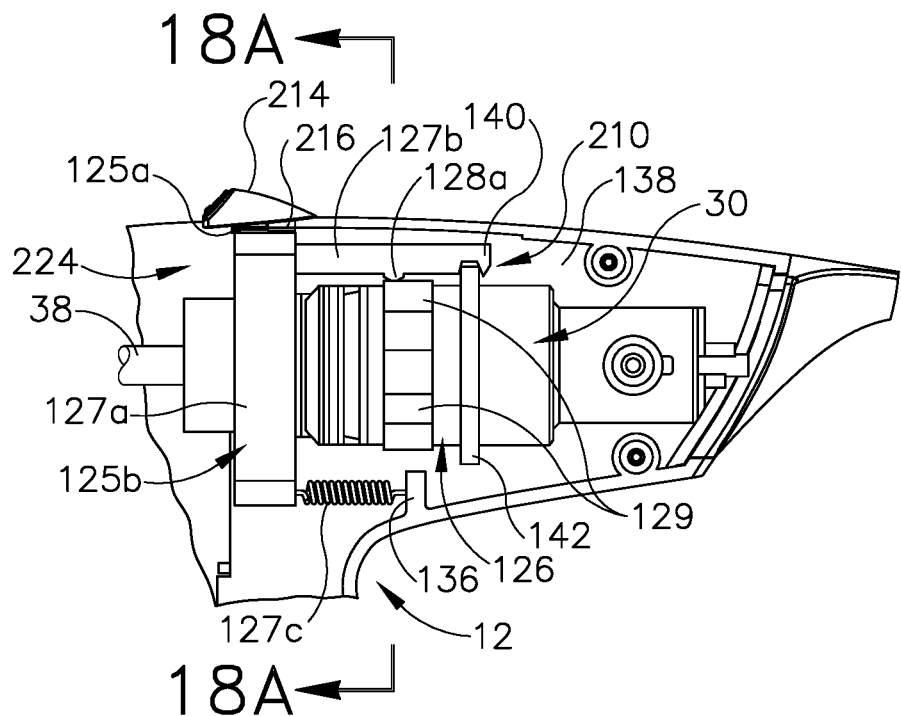
FIG. 17B depicts an enlarged side elevational view of the ultrasonic surgical instrument of FIG. 17A, showing the distal detent cam slip lock in a locked position.
Figure 18A:
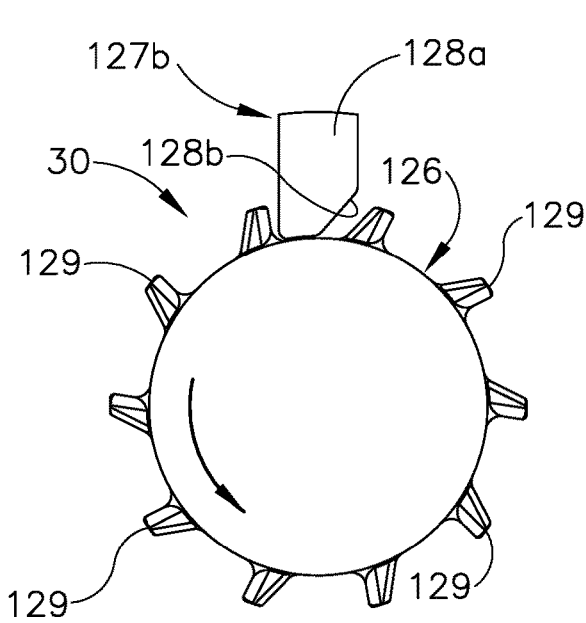
FIG. 18A depicts a cross-sectional view of the ultrasonic transducer assembly of FIG. 17A, taken along section line 18A-18A of FIG. 17B, showing the distal detent cam slip lock in the locked position.
Figure 18B:
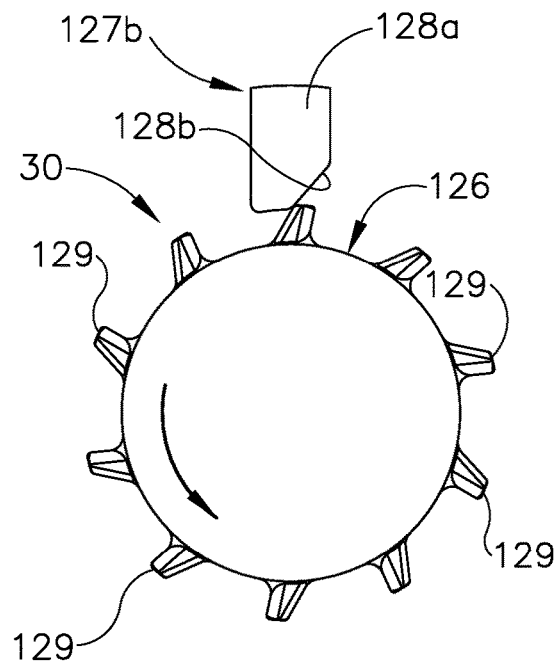
FIG. 18B depicts a cross-sectional view of the ultrasonic transducer assembly of FIG. 17A, taken along section line 18A-18A of FIG. 17B, showing the ultrasonic transducer assembly slipping relative to an arrester of the distal detent cam slip lock.
Figure 19:
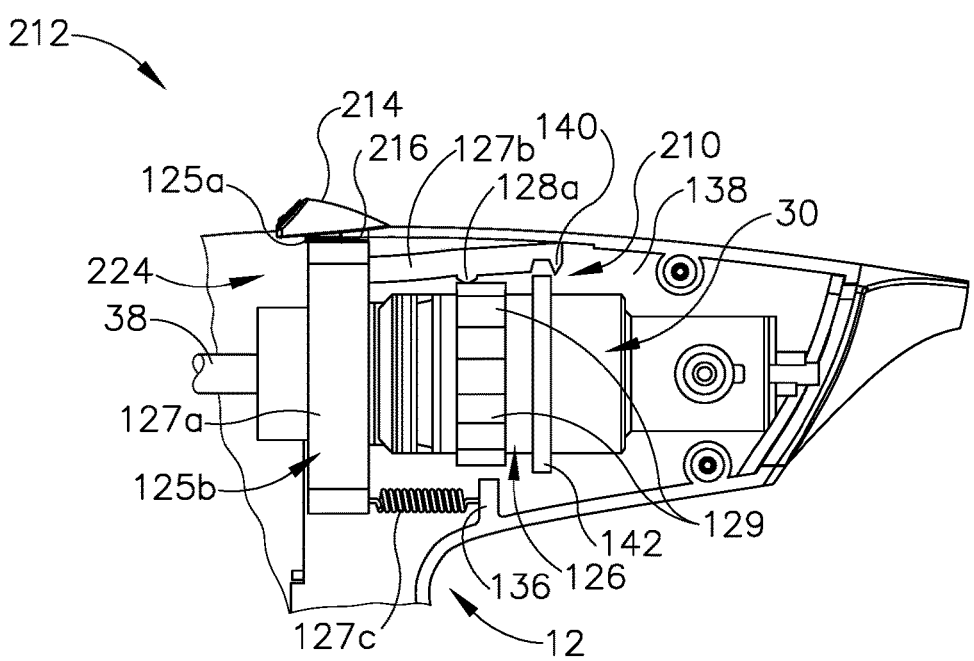
FIG. 19 depicts an enlarged side elevation view of the ultrasonic surgical instrument of FIG. 17A, with the distal detent cam slip lock returning from the locked position toward the unlocked position, but having various components removed for more clearly showing the distal detent cam slip lock.

FIGS. 17A-19 illustrate a second exemplary torque wrench in the form of a distal detent cam slip lock (210) of surgical instrument (212), which is configured to both inhibit rotation of transducer assembly (30) and limit torque applied to waveguide (38) to the predetermined torque. As shown in FIGS. 17A-17B, slip lock (210) includes a lock switch (214) extending through a lock channel (216) in body (18). More particularly, lock channel (216) extends longitudinally and transversely through an upper surface (90) of body (18) directly above the longitudinal axis. Lock switch (214) is thus longitudinally translatable between an unlocked position and a locked position for respectively unlocking and locking rotation of transducer assembly (30) relative to body (18). While lock switch (214) and lock channel (216) are positioned on upper surface (90) of body (18) of the present example, it will be appreciated that lock switch (214) and lock channel (216) may be alternatively positioned to cooperate with transducer assembly (30). The invention is thus not intended to be unnecessarily limited to having lock switch (214) and lock channel (216) positioned as shown herein.

Similar to proximal detent cam slip lock (110) discussed above with respect to FIGS. 5-16 and with like numbers indicating like features, slip lock (210) of FIGS. 17A-19 includes an arrester (224) having downward stem (125a) and arrester body (125b), which includes annular base (127a), cam arm (127b), and coil spring (127c). Cam arm (127b) has a catch cam (128a) with a catch surface (128b) that also are configured to engage the plurality of cam teeth (129), which extend radially outwardly from transducer can (126). In addition, detent latch (140) extends longitudinally from catch cam (128a) toward detent flange (142) for releasable securement therewith. However, unlike slip lock (210) (see FIG. 5), lock switch (214) is in a distal, unlocked position with arrester being in a distal, disengaged position, with each being configured to respectively translate proximally to a proximal, unlocked position and a proximal, engaged position, respectively. In turn, coil spring (127c) biases arrester (224) and lock switch (214) in a distal direction rather than in a proximal direction.

In an exemplary use, shaft assembly (14) is initially uncoupled from transducer assembly (30). The user translates lock switch (214) of slip lock (210) proximally from the unlocked position to the locked position such that catch surfaces (128b) of arrester (224) engage cam teeth (129) to seize rotation of transducer assembly (30) relative to body (18). Simultaneously, detent latch (140) releasably captures detent flange (142) in the longitudinal direction to inhibit relative longitudinal movement between arrester (224) and transducer assembly (30). The user then introduces proximal end portion of waveguide (38) to transducer assembly (30) and rotates knob (54) in a tightening direction to threadably engage the proximal end portion of waveguide (38) with transducer assembly (30) for tightening to the predetermined torque as described above in greater detail. Once reaching the predetermined torque, detent latch (140) radially clears detent flange (142) and coil spring (127c) urges arrester (124) from the engaged position to the disengaged position, thereby allowing cam teeth (129) to similarly clear catch cams (128a) and freely rotate relative to each other for inhibiting overtightening of waveguide (38) therein.

Figure 20A:
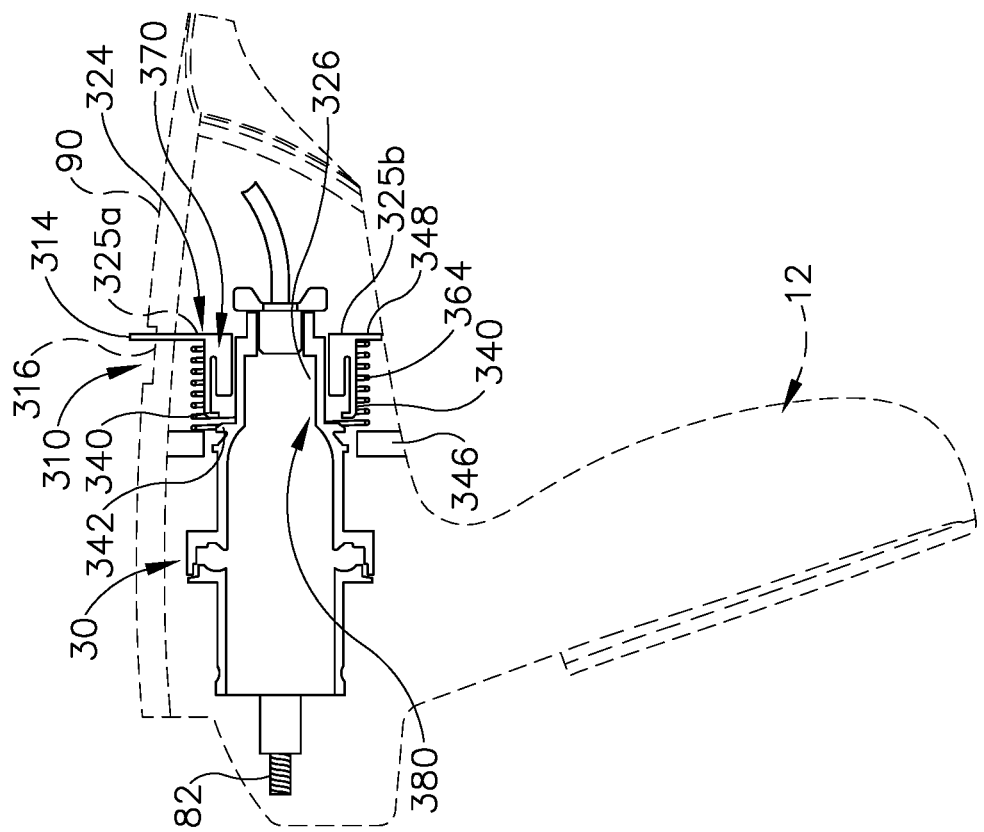
FIG. 20A depicts a side elevational view of a handle assembly of a fourth exemplary ultrasonic surgical instrument with a biased detent slip lock, but having various components removed for more clearly showing an ultrasonic transducer assembly and the biased detent slip lock in an unlocked position.
Figure 20B:
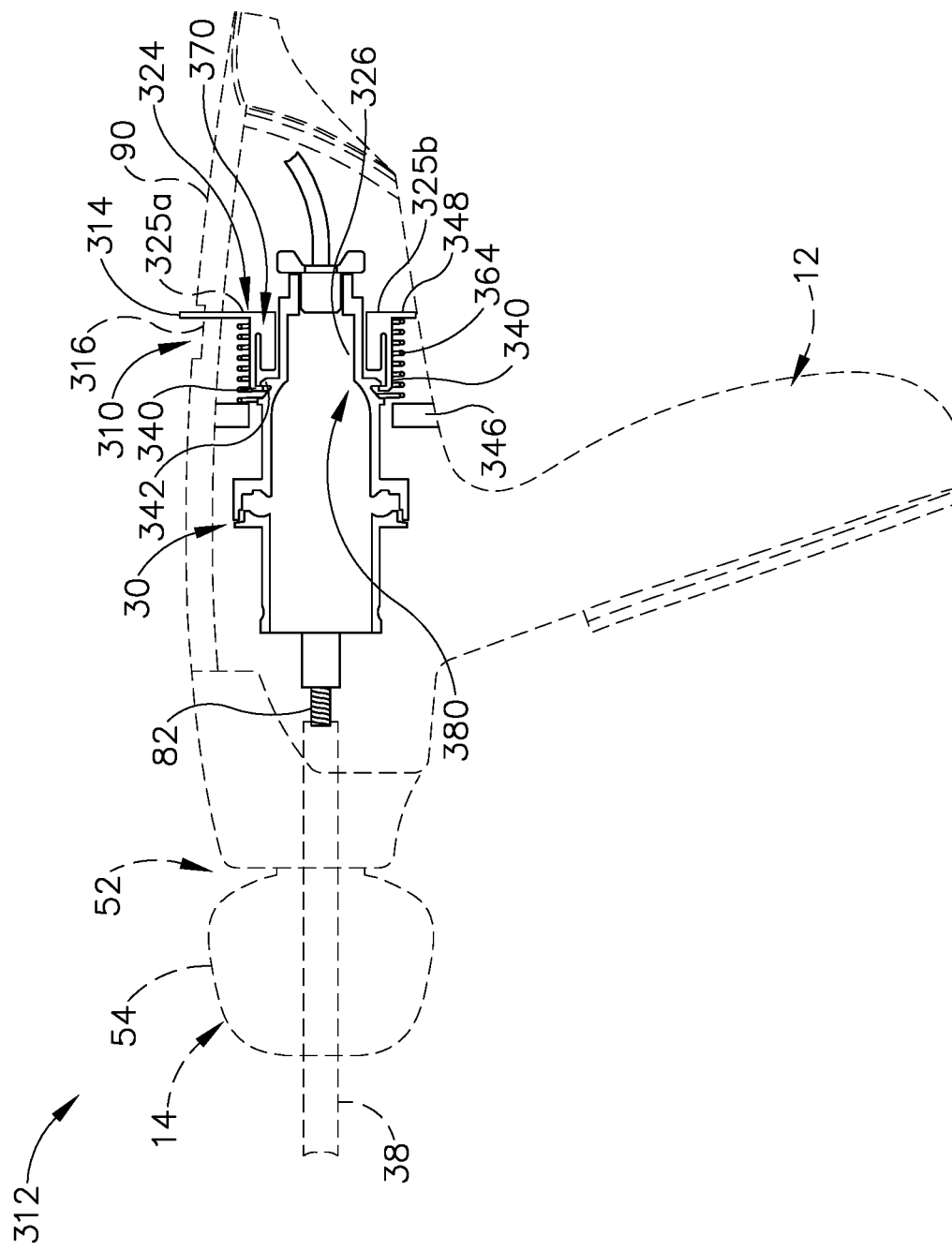
FIG. 20B depicts a side elevational view of the ultrasonic surgical instrument of FIG. 20A, with a shaft assembly urging the biased detent slip lock to a locked position relative to the ultrasonic transducer assembly in a proximal position.

Similar to proximal detent cam slip lock (110) discussed above with respect to FIGS. 5-16 and with like numbers indicating like features, slip lock (310) of FIGS. 20A-20B includes an arrester (324) having downward stem (125a) and arrester body (125b), which includes annular base (127a), cam arm (127b), and coil spring (127c). Cam arm (127b) has a catch cam (128a) with a catch surface (128b) that also are configured to engage the plurality of cam teeth (129), which extend radially outwardly from transducer can (126). In addition, detent latch (140) extends longitudinally from catch cam (128a) toward detent flange (142) for releasable securement therewith. However, unlike slip lock (210) (see FIG. 5), lock switch (214) is in a distal, unlocked position with arrester being in a distal, disengaged position, with each being configured to respectively translate proximally to a proximal, unlocked position and a proximal, engaged position, respectively. In turn, coil spring (127c) biases arrester (224) and lock switch (214) in a distal direction rather than in a proximal direction.

C. Exemplary Biased Detent Slip Lock

FIGS. 20A-22B illustrate a third exemplary torque wrench in the form of a biased detent slip lock (310) of surgical instrument (312), which is configured to both inhibit rotation of transducer assembly (30) and limit torque applied to waveguide (38) to the predetermined torque. As shown in FIGS. 20A-20B, slip lock (310) includes a lock switch (314) extending through a lock channel (316) in body (18). More particularly, lock channel (316) extends longitudinally and transversely through upper surface (90) of body (18) directly above the longitudinal axis. Lock switch (314) is thus longitudinally translatable between an unlocked position and a locked position for respectively unlocking and locking rotation of transducer assembly (30) relative to body (18). While lock switch (314) and lock channel (316) are positioned on upper surface (90) of body (18) of the present example, it will be appreciated that lock switch (314) and lock channel (316) may be alternatively positioned to cooperate with transducer assembly (30). The invention is thus not intended to be unnecessarily limited to having lock switch (314) and lock channel (316) positioned as shown herein.

Similar to proximal detent cam slip lock (110) discussed above with respect to FIGS. 5-16 and with like numbers indicating like features, slip lock (310) of FIGS. 20A-22B includes an arrester (324) having a downward stem (325a) and an arrester body (325b). In addition, arrester body (325b) generally surrounds a proximal portion of transducer assembly (30) and is configured to move distally relative to transducer assembly (30) for selectively inhibiting rotation of transducer assembly (30) relative to body (18) and limiting torque applied during coupling of waveguide (38) to the predetermined torque for proper installation. Unlike proximal detent cam slip lock (110) (see FIG. 5), slip lock (310) is configured to releasably secure to transducer assembly (30) upon proximal translation of transducer assembly (30) as shaft assembly (14) is introduced for installation. Accordingly, lock switch (314) does not require initial manipulation from the unlocked to the locked position since the proximal translation of transducer assembly (30) causes transducer assembly (30) to effectively move toward arrester (324) for locked securement, which is released upon application of the predetermined torque.

Slip lock (310) takes advantage of the initial proximal movement of transducer assembly (30) in some respects like an exemplary torque wrench assembly (not shown) described in greater detail in U.S. Pat. Pub. No. 2015/0245850, entitled "Ultrasonic Surgical Instrument with Removable Handle Assembly," published Sep. 3, 2015, issued as U.S. Pat. No. 10,010,340 on Jul. 3, 2018, the disclosure of which is incorporated by reference herein. Generally, slip lock (310) includes various features of the exemplary torque wrench assembly (not shown) such as a pawl ring (370), a drive member (380), and a coil spring (364) that have catch and deflectable portions for selectively inhibiting rotation of transducer assembly (30) relative to body (18) and limiting torque applied during coupling of waveguide (38) to the predetermined torque for proper installation.

Figure 21:
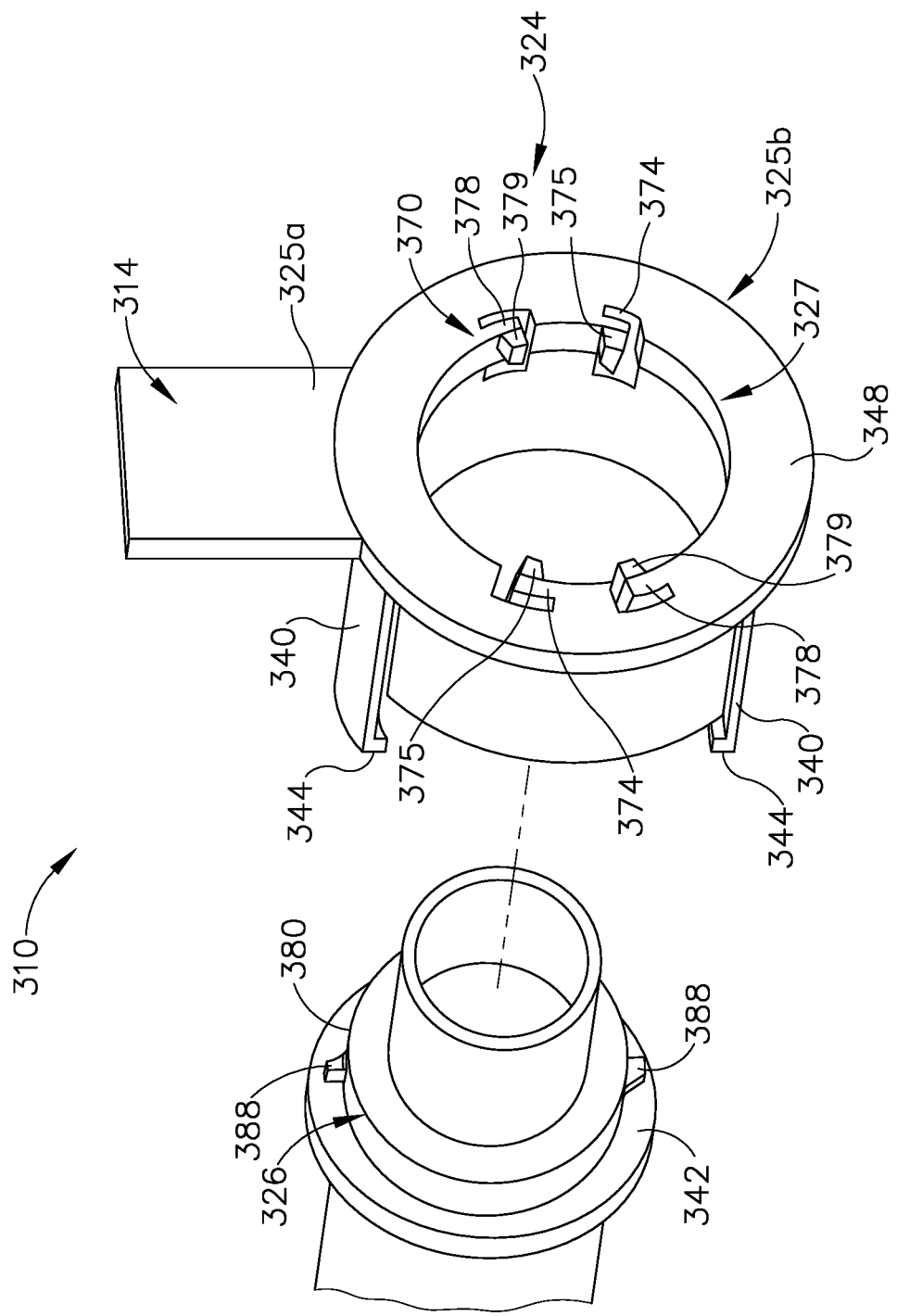
FIG. 21 depicts an exploded perspective view of the biased detent slip lock of FIG. 20A including an engagement collar, a detent flange, and an arrester.

To this end, and as shown in FIGS. 20B and 21, slip lock (310) includes an engagement feature (326) in the form of a transducer can (326) having a plurality of inner pawls (388) extending radially outwardly therefrom for releasable engagement with arrester (324). Arrester body (325b) of arrester (324) has the catch portion, which includes a pair of outer pawls (375, 379) and another pair of outer pawls (375, 379). Outer pawls (375, 379) extend radially inwardly from an annular, proximal base (327) of arrester body (325b) for cooperatively engaging inner pawls (388) of transducer can (326). The deflectable portion of arrester body (325b) includes a pair of resilient arms (374, 378) and another pair of resilient arms (374, 378). Outer pawls (375, 379) extend radially inwardly from resilient arms (374, 378), respectively, such that outer pawls (375, 379) deflect with resilient arms (374, 378) for limiting the transmission of torque between pawls (388, 378, 379) to the predetermined torque as discussed below in more detail. In other words, resilient arms (374, 378) are resiliently biased to assume the position shown in FIG. 21. However, resilient arms (374, 378) are configured to flex outwardly as will be described below in greater detail. As used herein, the term "pawls" may be used interchangeably with "catch cams" for reference to one or more various examples. The term "pawls" is thus not intended to unnecessarily limit the invention described herein.

Arrester (324) is further configured to releasably couple to transducer assembly (30) in the longitudinal direction to maintain longitudinal alignment between inner and outer pawls (388, 375, 379) for inhibiting relative rotation via respective catch surfaces therebetween. Arrester body (325b) thus includes a pair of resilient detent latches (340) extending distally from annular base (327) toward an annular detent flange (342), which extends annularly about transducer can (326) and is positioned distally from inner pawls (388). Detent latches (340) longitudinally capture annular detent flange (342) in the engaged position to longitudinally secure arrester (324) relative to transducer assembly (30) and cooperatively align inner and outer pawls (388, 375, 379) to inhibit relative rotation. To aid each detent latch (340) with capturing annular detent flange (342), each detent latch (340) has a distal cam surface (344) that deflects detent latch (340) resiliently outwardly to effectively hook detent latches (340) with the inward return of detent latches (340) as arrester (324) reaches the engaged position shown in FIG. 22A.

As shown in FIG. 20B, coil spring (364) is interposed between an integral boss mount (346) within body (18) and an outer annular flange mount (348) surrounding annular base (327) of arrester body (325b). Coil spring (364) is resiliently biased to urge arrester (324) and lock switch (314) proximally within body (18). Thus, as the unthreaded waveguide (38) pushes transducer assembly (30) proximally as shown in FIG. 20B, detent latches (340) longitudinally capture detent flange (342) to releasably secure arrester (324) to transducer can (326) in the longitudinal direction. Rotatably coupling waveguide (38) to threaded stud (82) effectively pulls transducer assembly (30) distally toward its typical operating position as shown in FIG. 22A and, in doing so, pulls arrester (324) and lock switch (314) distally therewith while arrester (324) inhibits relative rotation via pawls (388, 375, 379) as discussed above.

Figure 22A:
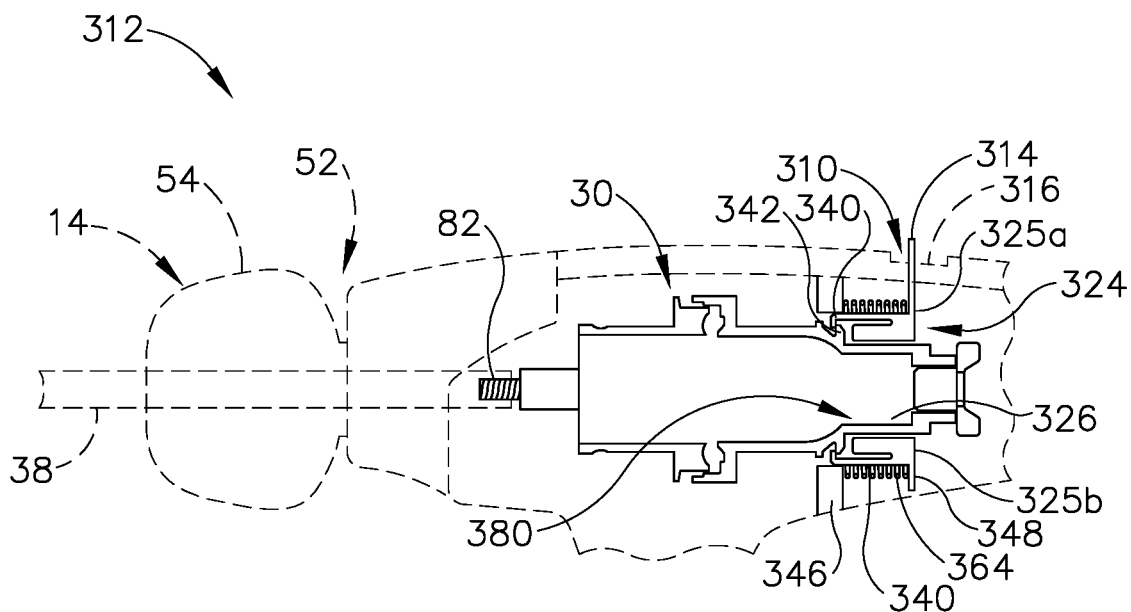
FIG. 22A depicts a cross-sectional side view of the biased detent slip lock of FIG. 20A with the biased detent slip lock in the locked position and the ultrasonic transducer assembly approaching the distal position with relative slip.
Figure 22B:
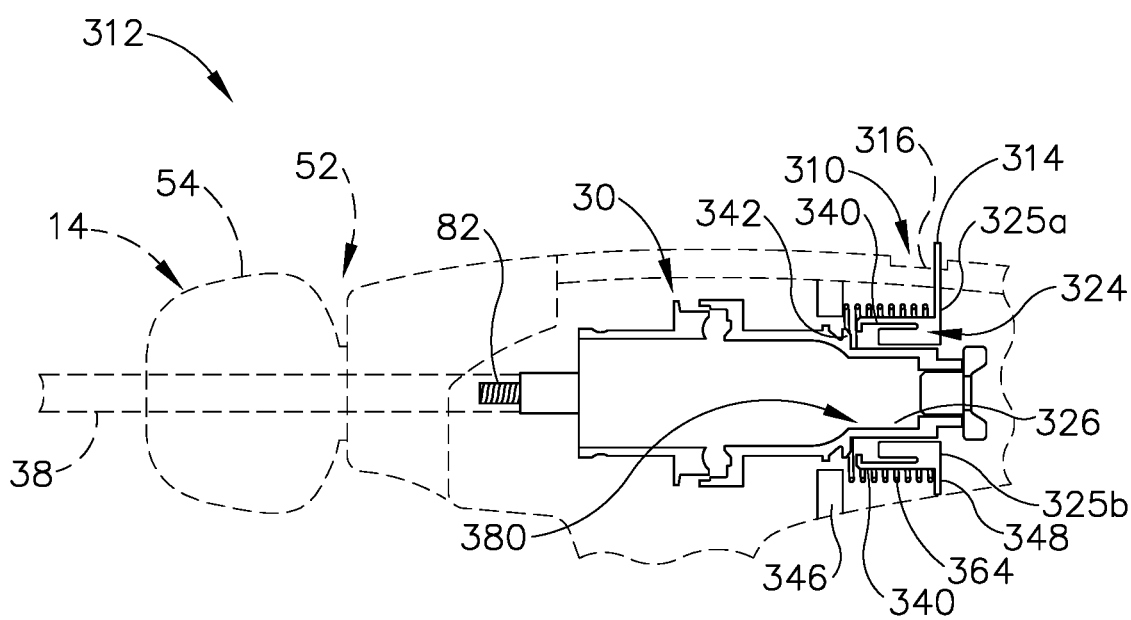
FIG. 22B depicts a cross-sectional side view of the biased detent slip lock of FIG. 20A with the ultrasonic transducer assembly in the distal position with the biased detent slip lock in the unlocked position relative to the ultrasonic transducer assembly.

As shown in FIGS. 22A and 22B, each resilient arm (374, 378) extends about the longitudinal axis and is cantilevered to outwardly deflect away from the longitudinal axis as the applied torque exceeds the predetermined torque. In addition, detent latches (340) extend distally from annular base (327) of arrester body (325b) as a cantilever and are also configured to outwardly deflect away from the longitudinal axis as coil spring (364) compresses due to distal movement. More particularly, the expansive proximal force of coil spring (364) increases with compression to effectively pull each detent latch (340) away from detent flange (342) until detent latches (340) resiliently deflect outwardly enough to clear detent flange (342) to thereby longitudinally release arrester (324) from transducer can (326).

Resilient arms (374, 378) and pawls (375, 379) are tuned to deflect enough to clear pawls (388) for relative slip at approximately the same time as coil spring (364) is tuned to force detent latches (340) to longitudinally release detent flange (342). Transducer can (326) with transducer assembly (30) may thus slip relative to pawls (375, 379) to inhibit overtightening waveguide (38) with transducer assembly (30) beyond the predetermined torque as shown in FIG. 22B. In the present example, resilient arms (374, 378) and outer pawls (375, 379) deflect outwardly together upon the application of such torque to allow for slippage beyond the predetermined torque to inhibit overtightening of waveguide (38) with transducer assembly (30). Detent latches (340) under the influence of coil spring (364) deflect independently, but simultaneously, of resilient arms (374, 378) and outer pawls (375, 379) in the present example.

In the event that alternative and/or additional mechanisms are incorporated into an alternative slip lock, it will be appreciated that similar tuning may be done in accordance with the invention. Alternatively, in another example, detent latches (340) may extend from resilient arms (374, 378) such that deflection occurs simultaneously and dependent on resilient arms (374, 378) to at least some extent. The invention is thus not intended to be unnecessarily limited to this exemplary arrangement of transducer can (326), resilient arms (374, 378), pawls (388, 375, 379), and detent latches (340).

In an exemplary use, shaft assembly (14) is initially uncoupled from transducer assembly (30). The user directs the proximal end portion of waveguide (38) against threaded stud (382) of transducer assembly (30) and forces transducer assembly (30) proximally to the locked position with slip lock (310) such that arrester (324) is in the engaged position therewith. Simultaneously, detent latches (340) releasably capture detent flange (342) in the longitudinal direction to inhibit relative longitudinal movement between arrester (324) and transducer assembly (30). The user then rotates knob (54) in a tightening direction to threadably engage the proximal end portion of waveguide (38) with transducer assembly (30) for tightening to the predetermined torque as described above in greater detail and pulling both transducer assembly (30) and arrester (324) distally within body (18).

Once reaching the predetermined torque, resilient arms (374, 378) and outer pawls (375, 379) deflect relative to inner pawls (388) for relative slip between transducer assembly (30) and arrester (324) to limit the applied torque to the predetermined torque. Simultaneously, coil spring (364) forces detent latch (340) to radially clear detent flange (342) and coil spring (364) urges arrester (324) from the engaged position to the disengaged position for using surgical instrument (312). In order to uncouple waveguide (38) from transducer assembly (30) with slip lock (310), the user manipulates lock switch (314) distally such that arrester (324) again engages transducer assembly (30) to limit relative rotation therebetween for removal of waveguide (38).

By way of further example, slippage of outer pawls (375, 378) relative to inner pawls (388) and the resilient return of resilient arms (374, 378) inward to their original position may also generate an audible indicator, a tactile indicator, or other signal to the user that waveguide (38) is coupled with transducer assembly (30) at the predetermined torque. Slip lock (310) may thus also provide an integral torque indicator for indicating to the user that waveguide (38) has been coupled to the transducer assembly (30) with the predetermined torque.

III. Handle Assembly with Torque Wrench Assembly and Lock Indicator

During use, the user selectively rotating waveguide (38) may not appreciate whether or not transducer assembly (30, 78) is in a locked state or an unlocked state with the above described slip locks (110, 210, 310) in locked or unlocked positions. It may thus be desirable to incorporate an integral lock indicator into one or more portions of surgical instruments (10, 112, 212, 312) for communicating a signal to the user that rotation of transducer assembly (30, 78) is inhibited from rotating relative to body (18), also referred to as the locked state; or free to rotate relative to body (18), also referred to as the unlocked state. One such lock indicator (410) is incorporated into a surgical instrument (412) described below in additional detail and illustrated in FIGS. 23-26C. In the present example, portions of lock indicator (410) are incorporated into a handle assembly (414). However, it will be appreciated that such portions may be alternatively positioned to communicate such signal. The invention is thus not intended to be unnecessarily limited to the specific arrangement of lock indicator (410) as shown herein. Furthermore, like numbers provided below indicate like features described above in additional detail.

Figure 23:
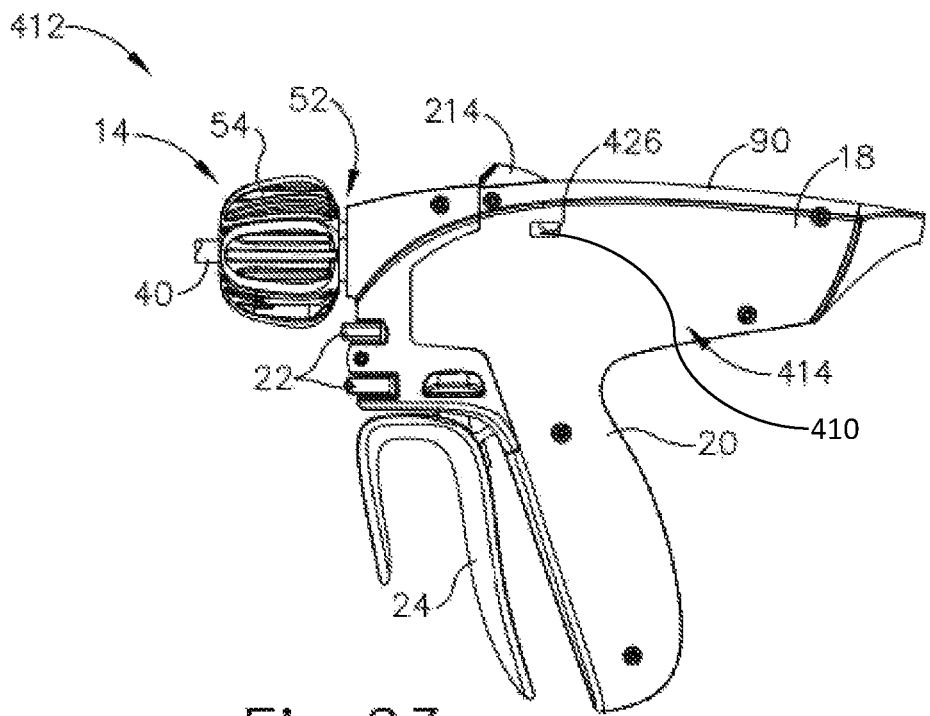
FIG. 23 depicts a side elevational view of a fifth exemplary ultrasonic surgical instrument with a torque wrench assembly having a lock indicator for indicating an unlocked position and a locked position.
Figure 24:
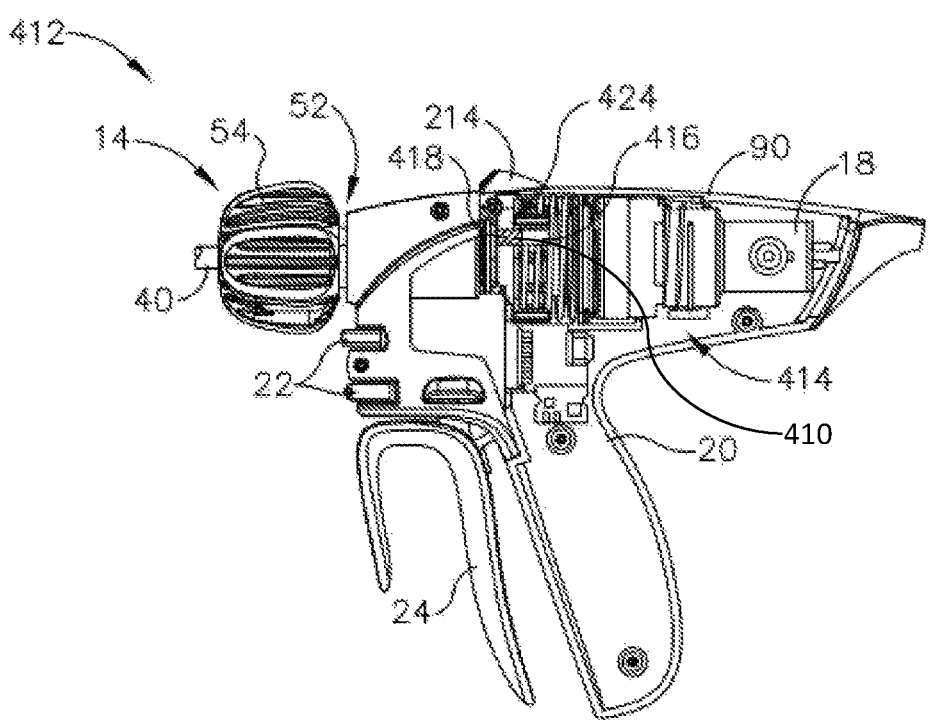
FIG. 24 depicts a side elevational view of the ultrasonic surgical instrument of FIG. 23, with various components removed for more clearly showing an ultrasonic transducer assembly and the torque wrench assembly in an unlocked position.
Figure 25:
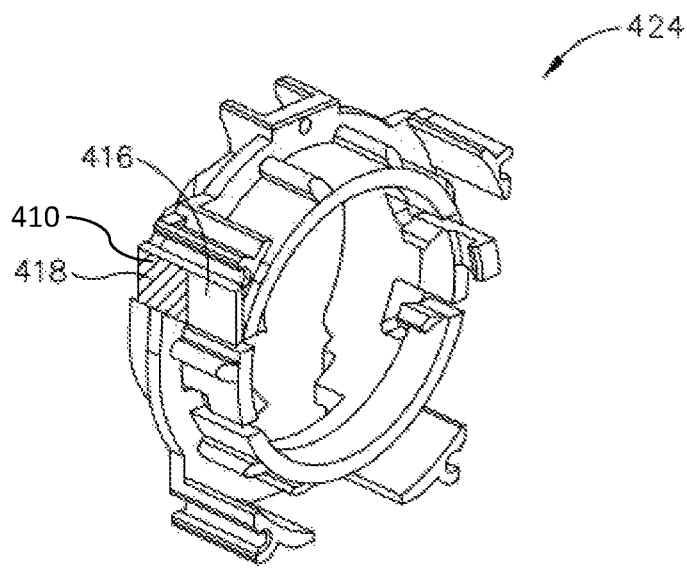
FIG. 25 depicts a perspective view of an arrestor of the torque wrench assembly of FIG. 23 having the lock indicator.

As seen in FIGS. 23-25, surgical instrument (412) includes visual lock indicator (410) configured to indicate the locked state of transducer assembly (30) to the user during use. Visual lock indicator (410) includes an unlocked indicia (416) positioned proximally from and adjacent to a locked indicia (418). In the present example, each of unlocked indicia (416) and locked indicia (418) are positioned directly on a portion of a torque wrench assembly, such as an arrester (424) to move with arrester (424) to indicate the locked state. To enable viewing of indicia (418, 420) on arrester (424), an indicia window (426) extends in alignment with indicia (418, 420) through body (18). Indicia window (426) aligns with unlocked indicia (416) and locked indicia (418), respectively, with lock switch (214) in the unlocked and locked states such that the operator may view unlocked indicia (416) and locked indicia (418) therethrough. While the particular alignment of indicia (416, 418) and indicia window (426) may be beneficial for viewing by a right-handed grip of handle assembly (414), it will be appreciated that similar features may be positioned on an opposite side of handle assembly (414) for more easily being viewed by an operator using a left-handed grip.

Figure 26A:
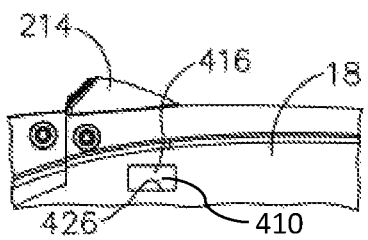
FIG. 26A depicts an enlarged side elevational view of the lock indicator of FIG. 23 in the unlocked position.
Figure 26B:
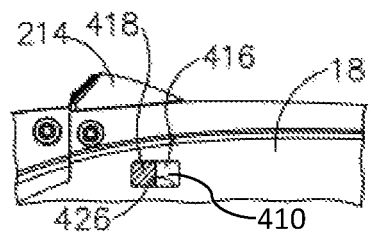
FIG. 26B depicts an enlarged side elevational view of the lock indicator of FIG. 23 moving from the unlocked position toward the locked position.
Figure 26C:
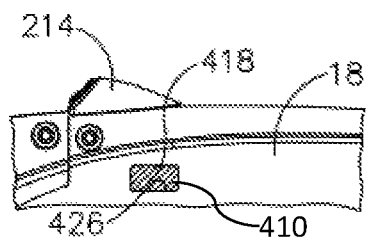
FIG. 26C depicts an enlarged side elevational view of the lock indicator of FIG. 23 in the locked position.

In an exemplary use, and as shown in succession in FIGS. 26A-26C, unlocked indicia (416) indicates that transducer assembly (30) is inhibited from rotation relative to body (18). More particularly, arrester (424) in the unlocked state is disengaged from transducer assembly (30) to allow transducer assembly (30) to rotate freely relative to body (18). Manipulating lock switch (214) proximally from the unlocked position toward the locked position forces lock indicator (410) to translate proximally such that locked indicia (418) is visible through window (426). Accordingly, arrester (424) engages transducer assembly (30) in the engaged position such that transducer assembly is in the locked state. Returning lock switch (214) distally to the unlocked position similarly returns locked indicia (418) for viewing through window (426) to indicate that transducer assembly is also in the unlocked state.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) an instrument body; (b) an ultrasonic transducer assembly rotatably mounted along a longitudinal axis within the instrument body; and (c) a slip lock operatively connected to the instrument body and including an arrester, wherein the arrester is configured to move relative to the ultrasonic transducer assembly between an engaged position and a disengaged position, the arrester having a catch portion and a deflectable portion, wherein the deflectable portion is configured to deflect relative to the ultrasonic transducer assembly, wherein the ultrasonic transducer assembly is configured to be selectively rotated about the longitudinal axis relative to the instrument body with the arrester in the disengaged position, wherein the catch portion is configured to seize the ultrasonic transducer assembly in the engaged position to thereby inhibit rotation about the longitudinal axis relative to the instrument body for rotatably coupling with the acoustic waveguide up to a predetermined torque, and wherein the deflectable portion is configured to deflect relative to the ultrasonic transducer assembly upon receiving a torque greater than the predetermined torque such that the catch portion releases the ultrasonic transducer assembly to slip relative to the catch portion for limiting coupling of the ultrasonic transducer assembly with the acoustic waveguide to the predetermined torque.

Example 2

The surgical instrument of Example 1, wherein the arrester and the ultrasonic transducer assembly are configured to move longitudinally relative to each other between the engaged and disengaged positions for longitudinal engagement therebetween.

Example 3

The surgical instrument of Example 2, wherein the arrester is configured to move distally relative to the ultrasonic transducer assembly from the disengaged position toward the engaged position.

Example 4

The surgical instrument of Example 2, wherein the arrester is configured to move proximally relative to the ultrasonic transducer assembly from the disengaged position toward the engaged position.

Example 5

The surgical instrument of any one or more of Examples 1 through 4, wherein the instrument body includes a switch channel, wherein the slip lock includes a lock switch extending through the switch channel and operatively connected to the arrester, wherein the lock switch is configured to be selectively moved between an unlocked position and a locked position thereby selectively moving the arrester relative to the ultrasonic transducer assembly between the disengaged and engaged positions.

Example 6

The surgical instrument of any one or more of Examples 1 through 5, further comprising a lock indicator operatively connected to the slip lock, wherein the lock indicator is configured to indicate to a user that the catch portion has seized the ultrasonic transducer assembly in the engaged position.

Example 7

The surgical instrument of any one or more of Examples 1 through 6, wherein the slip lock further includes an engagement feature connected to the ultrasonic transducer assembly, and wherein the catch portion of the arrester is configured to engage the engagement feature in the engaged position to inhibit rotation of the ultrasonic transducer assembly.

Example 8

The surgical instrument of Example 7, wherein the engagement feature includes a plurality of teeth, wherein the plurality of teeth is positioned angularly about the ultrasonic transducer assembly, wherein the teeth project radially outwardly relative to the transducer assembly, and wherein the catch portion of the arrester is configured to be received between the plurality of teeth in the engaged position thereby inhibiting rotation of the engagement feature and the ultrasonic transducer assembly connected thereto up to the predetermined torque.

Example 9

The surgical instrument of Example 8, wherein the catch portion of the arrester extends from the deflectable portion of the arrester to the plurality of teeth of the engagement feature in the engaged position to thereby releasably secure the catch portion of the arrester between the plurality of teeth for inhibiting rotation of the ultrasonic transducer assembly, and wherein the engagement feature with torque applied greater than the predetermined torque is configured to thereby deflect the deflectable portion of the arrester to release the plurality of teeth such that the engagement feature and the ultrasonic transducer assembly slip relative to the catch portion.

Example 10

The surgical instrument of Example 9, wherein the deflectable portion includes a catch arm and the catch portion includes a catch cam such that the catch cam extends from the catch arm and is configured to deflect with the catch arm, wherein each of the plurality of teeth is configured to urge the catch cam therewith upon the ultrasonic transducer assembly receiving torque greater than the predetermined torque such that the catch arm resiliently deflects with the catch cam until the catch cam releases the engagement feature and the ultrasonic transducer assembly slips relative to the catch cam for limiting coupling of the ultrasonic transducer assembly with the acoustic waveguide to the predetermined torque.

Example 11

The surgical instrument of Example 10, wherein the slip lock further includes a transducer detent feature connected to the ultrasonic transducer assembly, wherein the arrester further includes an arrester detent feature, and wherein the arrester detent feature and the transducer detent feature are configured to engage with the arrester in the engaged position to releasably secure the arrester to the ultrasonic transducer assembly in a longitudinal direction.

Example 12

The surgical instrument of any one or more of Examples 1 through 11, wherein the slip lock further includes a transducer detent feature connected to the ultrasonic transducer assembly, wherein the arrester further includes an arrester detent feature, and wherein the arrester detent feature and the transducer detent feature are configured to engage with the arrester in the engaged position to releasably secure the arrester to the ultrasonic transducer assembly in a longitudinal direction.

Example 13

The surgical instrument of Example 12, wherein the catch portion of the arrester, the deflectable portion of the arrester, and the arrester detent feature are configured to collectively deflect together relative to the ultrasonic transducer assembly such that deflection of the deflectable portion thereby moves the arrester detent feature therewith to disengage the arrester detent feature from the transducer detent feature.

Example 14

The surgical instrument of Example 13, wherein the arrester is biased toward the disengaged position such that the arrester is configured to resiliently return from the engaged position toward the disengaged position as the arrester detent feature disengages from the transducer detent feature.

Example 15

The surgical instrument of any one or more of Examples 12 through 14, wherein the slip lock further includes a biasing element, wherein the biasing element biases the arrester from the engaged position toward the disengaged position, and wherein the biasing element is configured to overcome the engagement between the arrester detent feature and the transducer detent feature as the ultrasonic transducer assembly receives applied torque greater than the predetermined torque and direct the arrester toward the disengaged position.

Example 16

A surgical instrument, comprising: (a) an instrument body; (b) an ultrasonic transducer assembly rotatably mounted along a longitudinal axis within the instrument body; and (c) a slip lock operatively connected to the instrument body and configured to selectively move between a disengaged position and an engaged position, wherein the ultrasonic transducer assembly is configured to be selectively rotatable about the longitudinal axis in the disengaged position, wherein the slip lock includes: (i) an engagement feature secured to the ultrasonic transducer assembly such that the engagement feature rotates with the ultrasonic transducer feature, (ii) a catch arm configured to resiliently deflect, (iii) a catch cam extending from the catch arm and configured to deflect with the catch arm, wherein the catch cam is configured to engage the engagement feature with the slip lock in the engaged position to thereby selectively inhibit rotation of the engagement feature and the ultrasonic transducer assembly about the longitudinal axis for rotatably coupling with the acoustic waveguide up to a predetermined torque, (iv) a transducer detent feature connected to the ultrasonic transducer assembly, and (v) an arrester detent feature projecting from the catch cam toward the transducer detent feature, wherein the arrester detent feature and the transducer detent feature are configured to engage with the arrester in the engaged position to releasably secure the arrester to the ultrasonic transducer assembly in a longitudinal direction, wherein the engagement feature is configured to urge the catch cam therewith upon the ultrasonic transducer assembly receiving a torque greater than the predetermined torque such that the catch arm and the arrester detent feature resiliently deflect with the catch cam until the catch cam and the arrester detent feature respectively release the engagement feature and the transducer detent feature such that the ultrasonic transducer assembly slips relative to the catch cam for limiting coupling of the ultrasonic transducer assembly with the acoustic waveguide to the predetermined torque.

Example 17

The surgical instrument of Example 16, wherein the arrester is biased toward the disengaged position such that the arrester is configured to resiliently return from the engaged position toward the disengaged position as the arrester detent feature disengages from the transducer detent feature.

Example 18

The surgical instrument of Example 17, wherein the transducer detent feature comprises an annular flange extending angularly about the ultrasonic transducer assembly, and wherein the arrester detent feature comprises a latch extending from the catch cam toward the annular flange.

Example 19

A surgical instrument, comprising: (a) an instrument body; (b) an ultrasonic transducer assembly rotatably mounted along a longitudinal axis within the instrument body; and (c) a slip lock operatively connected to the instrument body and configured to selectively move between a disengaged position and an engaged position, wherein the ultrasonic transducer assembly is configured to be selectively rotatable about the longitudinal axis in the disengaged position, wherein the slip lock includes: (i) an engagement feature secured to the ultrasonic transducer assembly such that the engagement feature rotates with the ultrasonic transducer feature, (ii) a catch arm configured to resiliently deflect, (iii) a catch cam extending from the catch arm and configured to deflect with the catch arm, wherein the catch cam is configured to engage the engagement feature with the slip lock in the engaged position to thereby selectively inhibit rotation of the engagement feature and the ultrasonic transducer assembly about the longitudinal axis for rotatably coupling with the acoustic waveguide up to a predetermined torque, (iv) a transducer detent feature connected to the ultrasonic transducer assembly, (v) an arrester detent feature projecting toward the transducer detent feature, wherein the arrester detent feature and the transducer detent feature are configured to engage with the arrester in the engaged position to releasably secure the arrester to the ultrasonic transducer assembly in a longitudinal direction, and (vi) a biasing element configured to biasing the arrester toward the disengaged position, wherein the engagement feature is configured to urge the catch cam therewith upon the ultrasonic transducer assembly receiving a torque greater than the predetermined torque such that the catch arm resiliently deflects with the catch cam until the catch cam respectively releases the engagement feature and the ultrasonic transducer assembly slips relative to the catch cam for limiting coupling of the ultrasonic transducer assembly with the acoustic waveguide to the predetermined torque, and wherein the biasing element is configured to overcome the engagement between the arrester detent feature and the transducer detent feature as the ultrasonic transducer assembly receives applied torque greater than the predetermined torque and direct the arrester toward the disengaged position.

Example 20

The surgical instrument of Example 19, wherein the transducer detent feature comprises an annular flange extending angularly about the ultrasonic transducer assembly, and wherein the arrester detent feature comprises a latch extending from the catch cam toward the annular flange.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) an instrument body;
   (b) an ultrasonic transducer assembly rotatably mounted along a longitudinal axis within the instrument body; and
   (c) a slip lock operatively connected to the instrument body and including an arrester, wherein the arrester is configured to move relative to the ultrasonic transducer assembly between an engaged position and a disengaged position, the arrester having a catch portion and a deflectable portion, wherein the deflectable portion is configured to deflect relative to the ultrasonic transducer assembly, wherein the ultrasonic transducer assembly is configured to be selectively rotated about the longitudinal axis relative to the instrument body with the arrester in the disengaged position, wherein the ultrasonic transducer assembly is configured to be longitudinally fixed relative to the arrester with the arrester in the engaged position, wherein the catch portion is configured to seize the ultrasonic transducer assembly in the engaged position to thereby inhibit rotation about the longitudinal axis relative to the instrument body for rotatably coupling with the acoustic waveguide up to a predetermined torque, and wherein the deflectable portion is configured to deflect relative to the ultrasonic transducer assembly upon receiving a torque greater than the predetermined torque such that the catch portion releases the ultrasonic transducer assembly to slip relative to the catch portion for limiting coupling of the ultrasonic transducer assembly with the acoustic waveguide to the predetermined torque.

2. The surgical instrument of claim 1, wherein the arrester and the ultrasonic transducer assembly are configured to move longitudinally relative to each other between the engaged and disengaged positions for longitudinal engagement therebetween.

3. The surgical instrument of claim 2, wherein the arrester is configured to move distally relative to the ultrasonic transducer assembly from the disengaged position toward the engaged position.

4. The surgical instrument of claim 2, wherein the arrester is configured to move proximally relative to the ultrasonic transducer assembly from the disengaged position toward the engaged position.

5. The surgical instrument of claim 1, wherein the instrument body includes a switch channel, wherein the slip lock includes a lock switch extending through the switch channel and operatively connected to the arrester, wherein the lock switch is configured to be selectively moved between an unlocked position and a locked position thereby selectively moving the arrester relative to the ultrasonic transducer assembly between the disengaged and engaged positions.

6. The surgical instrument of claim 1, further comprising a lock indicator operatively connected to the slip lock, wherein the lock indicator is configured to indicate to a user that the catch portion has seized the ultrasonic transducer assembly in the engaged position.

7. The surgical instrument of claim 1, wherein the slip lock further includes an engagement feature connected to the ultrasonic transducer assembly, and wherein the catch portion of the arrester is configured to engage the engagement feature in the engaged position to inhibit rotation of the ultrasonic transducer assembly.

8. The surgical instrument of claim 7, wherein the engagement feature includes a plurality of teeth, wherein the plurality of teeth is positioned angularly about the ultrasonic transducer assembly, wherein the teeth project radially outwardly relative to the transducer assembly, and wherein the catch portion of the arrester is configured to be received between the plurality of teeth in the engaged position thereby inhibiting rotation of the engagement feature and the ultrasonic transducer assembly connected thereto up to the predetermined torque.

9. The surgical instrument of claim 8, wherein the catch portion of the arrester extends from the deflectable portion of the arrester to the plurality of teeth of the engagement feature in the engaged position to thereby releasably secure the catch portion of the arrester between the plurality of teeth for inhibiting rotation of the ultrasonic transducer assembly, and wherein the engagement feature with torque applied greater than the predetermined torque is configured to thereby deflect the deflectable portion of the arrester to release the plurality of teeth such that the engagement feature and the ultrasonic transducer assembly slip relative to the catch portion.

10. The surgical instrument of claim 9, wherein the deflectable portion includes a catch arm and the catch portion includes a catch cam such that the catch cam extends from the catch arm and is configured to deflect with the catch arm, wherein each of the plurality of teeth is configured to urge the catch cam therewith upon the ultrasonic transducer assembly receiving torque greater than the predetermined torque such that the catch arm resiliently deflects with the catch cam until the catch cam releases the engagement feature and the ultrasonic transducer assembly slips relative to the catch cam for limiting coupling of the ultrasonic transducer assembly with the acoustic waveguide to the predetermined torque.

11. The surgical instrument of claim 10, wherein the slip lock further includes a transducer detent feature connected to the ultrasonic transducer assembly, wherein the arrester further includes an arrester detent feature, and wherein the arrester detent feature and the transducer detent feature are configured to engage with the arrester in the engaged position to releasably secure the arrester to the ultrasonic transducer assembly in a longitudinal direction.

12. The surgical instrument of claim 1, wherein the slip lock further includes a transducer detent feature connected to the ultrasonic transducer assembly, wherein the arrester further includes an arrester detent feature, and wherein the arrester detent feature and the transducer detent feature are configured to engage with the arrester in the engaged position to releasably secure the arrester to the ultrasonic transducer assembly in a longitudinal direction.

13. The surgical instrument of claim 12, wherein the catch portion of the arrester, the deflectable portion of the arrester, and the arrester detent feature are configured to collectively deflect together relative to the ultrasonic transducer assembly such that deflection of the deflectable portion thereby moves the arrester detent feature therewith to disengage the arrester detent feature from the transducer detent feature.

14. The surgical instrument of claim 13, wherein the arrester is biased toward the disengaged position such that the arrester is configured to resiliently return from the engaged position toward the disengaged position as the arrester detent feature disengages from the transducer detent feature.

15. The surgical instrument of claim 12, wherein the slip lock further includes a biasing element, wherein the biasing element biases the arrester from the engaged position toward the disengaged position, and wherein the biasing element is configured to overcome the engagement between the arrester detent feature and the transducer detent feature as the ultrasonic transducer assembly receives applied torque greater than the predetermined torque and direct the arrester toward the disengaged position.

16. The surgical instrument of claim 1, wherein the slip lock further includes an engagement feature connected to the ultrasonic transducer assembly, wherein the catch portion of the arrester is configured to engage the engagement feature in the engaged position to inhibit rotation of the ultrasonic transducer assembly, wherein the catch portion of the arrester is configured to be received against the engagement feature in the engaged position thereby inhibiting rotation of the engagement feature and the ultrasonic transducer assembly connected thereto up to the predetermined torque, wherein the catch portion of the arrester extends from the deflectable portion of the arrester to the engagement feature in the engaged position to thereby releasably secure the catch portion of the arrester against the engagement feature for inhibiting rotation of the ultrasonic transducer assembly, and wherein the engagement feature with torque applied greater than the predetermined torque is configured to thereby deflect the deflectable portion of the arrester to release the engagement feature such that the engagement feature and the ultrasonic transducer assembly slip relative to the catch portion.

17. The surgical instrument of claim 1, wherein the ultrasonic transducer assembly is further configured to be longitudinally fixed relative to the instrument body with the arrester in the engaged position.

18. A surgical instrument, comprising:
(a) an instrument body;
(b) an ultrasonic transducer assembly rotatably mounted along a longitudinal axis within the instrument body; and
(c) a slip lock operatively connected to the instrument body and configured to selectively move between a disengaged position and an engaged position, wherein the ultrasonic transducer assembly is configured to be selectively rotatable about the longitudinal axis in the disengaged position, wherein the slip lock includes:
 (i) an engagement feature secured to the ultrasonic transducer assembly such that the engagement feature rotates with the ultrasonic transducer feature,
 (ii) a catch arm configured to resiliently deflect,
 (iii) a catch cam extending from the catch arm and configured to deflect with the catch arm, wherein the catch cam is configured to engage the engagement feature with the slip lock in the engaged position to thereby selectively inhibit rotation of the engagement feature and the ultrasonic transducer assembly about the longitudinal axis for rotatably coupling with the acoustic waveguide up to a predetermined torque,
 (iv) a transducer detent feature connected to the ultrasonic transducer assembly, and
 (v) an arrester detent feature projecting from the catch cam toward the transducer detent feature, wherein the arrester detent feature and the transducer detent feature are configured to engage with the arrester detent feature in the engaged position to releasably secure the arrester detent feature to the ultrasonic transducer assembly in a longitudinal direction such that the ultrasonic transducer assembly is longitudinally fixed relative to the arrester detent feature and the instrument body while engaged therewith,
wherein the engagement feature is configured to urge the catch cam therewith upon the ultrasonic transducer assembly receiving a torque greater than the predetermined torque such that the catch arm and the arrester detent feature resiliently deflect with the catch cam until the catch cam and the arrester detent feature respectively release the engagement feature and the transducer detent feature such that the ultrasonic transducer assembly slips relative to the catch cam for limiting coupling of the ultrasonic transducer assembly with the acoustic waveguide to the predetermined torque.

19. The surgical instrument of claim 18, wherein the arrester is biased toward the disengaged position such that the arrester is configured to resiliently return from the engaged position toward the disengaged position as the arrester detent feature disengages from the transducer detent feature.

20. A surgical instrument, comprising:
(a) an instrument body;
(b) an ultrasonic transducer assembly rotatably mounted along a longitudinal axis within the instrument body; and
(c) a slip lock operatively connected to the instrument body and configured to selectively move between a disengaged position and an engaged position, wherein the ultrasonic transducer assembly is configured to be selectively rotatable about the longitudinal axis in the disengaged position, wherein the slip lock includes:
 (i) an engagement feature secured to the ultrasonic transducer assembly such that the engagement feature rotates with the ultrasonic transducer feature,
 (ii) a catch arm configured to resiliently deflect,
 (iii) a catch cam extending from the catch arm and configured to deflect with the catch arm, wherein the catch cam is configured to engage the engagement feature with the slip lock in the engaged position to thereby selectively inhibit rotation of the engagement feature and the ultrasonic transducer assembly about the longitudinal axis for rotatably coupling with the acoustic waveguide up to a predetermined torque,
 (iv) a transducer detent feature connected to the ultrasonic transducer assembly,
 (v) an arrester detent feature projecting toward the transducer detent feature, wherein the arrester detent feature and the transducer detent feature are configured to engage with the arrester detent feature in the engaged position to releasably secure the arrester detent feature to the ultrasonic transducer assembly in a longitudinal direction such that the ultrasonic transducer assembly is longitudinally fixed relative to the arrester detent feature and the instrument body while engaged therewith, and
 (vi) a biasing element configured to bias the arrester toward the disengaged position,
wherein the engagement feature is configured to urge the catch cam therewith upon the ultrasonic transducer assembly receiving a torque greater than the predetermined torque such that the catch arm resiliently deflects with the catch cam until the catch cam respectively releases the engagement feature and the ultrasonic transducer assembly slips relative to the catch cam for limiting coupling of the ultrasonic transducer assembly with the acoustic waveguide to the predetermined torque, and
wherein the biasing element is configured to overcome the engagement between the arrester detent feature and the transducer detent feature as the ultrasonic transducer assembly receives applied torque greater than the predetermined torque and direct the arrester toward the disengaged position.

\* \* \* \* \*